(12) United States Patent
Henry et al.

(10) Patent No.: US 12,207,832 B2
(45) Date of Patent: *Jan. 28, 2025

(54) METHOD FOR PERCUTANEOUS TREATMENT OF VESSELS

(71) Applicant: Signati Medical Inc., Providence, RI (US)

(72) Inventors: Gerard Henry, Shreveport, LA (US); Robert A. Van Wyk, St. Pete Beach, FL (US)

(73) Assignee: Signati Medical Inc., Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/492,015

(22) Filed: Oct. 23, 2023

(65) Prior Publication Data

US 2024/0050115 A1     Feb. 15, 2024

Related U.S. Application Data

(63) Continuation-in-part of application No. 18/341,375, filed on Jun. 26, 2023, which is a continuation of application No. 17/709,675, filed on Mar. 31, 2022, now Pat. No. 11,723,680, which is a continuation-in-part of application No. 16/700,393, filed on Dec. 2, 2019, now Pat. No. 11,291,581, and a continuation-in-part of application No. 17/338,115, (Continued)

(51) Int. Cl.
*A61B 17/28* (2006.01)
*A61F 6/20* (2006.01)

(52) U.S. Cl.
CPC .............. *A61B 17/282* (2013.01); *A61F 6/20* (2013.01); *A61B 2017/2808* (2013.01)

(58) Field of Classification Search
CPC ... A61B 17/282; A61B 17/30; A61B 17/2812; A61B 2017/2808; A61B 2017/00349; A61B 2017/2837; A61B 2017/305; A61B 18/1442; A61B 2018/00547; A61B 2018/126; A61F 6/20
See application file for complete search history.

(56) References Cited

U.S. PATENT DOCUMENTS

| 3,762,417 A | 10/1973 | Textor |
| 4,803,983 A | 2/1989 | Siegel |

(Continued)

*Primary Examiner* — Ronald Hupczey, Jr.
(74) *Attorney, Agent, or Firm* — Smith Patent, LLC; Chalin A. Smith

(57) ABSTRACT

Conventional varicose vein techniques suffer from a number of disadvantages and potential complications, including, for example, a risk for the development of hematomas, swelling, and blood clots, post-surgical pain and nerve injury, a potential for spontaneous regeneration and undesired resumption of varicosity, a need for a highly skilled surgical professional, as well as, in certain instances, a prolonged recovery period, accompanied by severe limitations on post-surgical activity. The present invention overcomes the disadvantages and deficiencies of the prior art by providing a method for percutaneously occluding and dividing a varicose vein or other problematic vessel, a rapid, reliable, less invasive therapy that may be readily, reliably, and successfully performed by minimally skilled personnel around the world in a variety of medical settings.

22 Claims, 23 Drawing Sheets

Related U.S. Application Data filed on Jun. 3, 2021, now Pat. No. 11,291,493, which is a continuation-in-part of application No. 17/150,313, filed on Jan. 15, 2021, now abandoned, which is a continuation-in-part of application No. 16/700,393, filed on Dec. 2, 2019, now Pat. No. 11,291,581.

(60) Provisional application No. 63/475,193, filed on Oct. 21, 2022, provisional application No. 62/995,188, filed on Jan. 16, 2020, provisional application No. 62/917,325, filed on Dec. 3, 2018.

(56) References Cited

U.S. PATENT DOCUMENTS

| | | | |
|---|---|---|---|
| 4,920,982 A | 5/1990 | Goldstein | |
| 5,026,379 A | 6/1991 | Yoon | |
| 5,203,785 A | 4/1993 | Slater | |
| 5,445,638 A | 8/1995 | Rydell et al. | |
| 5,667,518 A | 9/1997 | Pannell | |
| 5,702,390 A | 12/1997 | Austin et al. | |
| 5,797,958 A * | 8/1998 | Yoon | A61B 17/3417 |
| | | | 606/139 |
| 5,827,279 A | 10/1998 | Hughett et al. | |
| 5,865,835 A | 2/1999 | Lolagne | |
| 5,891,141 A | 4/1999 | Rydell | |
| 5,972,002 A | 10/1999 | Bark | |
| 6,610,060 B2 | 8/2003 | Mulier et al. | |
| 6,843,789 B2 | 1/2005 | Goble | |
| 8,220,464 B2 | 7/2012 | Pannell et al. | |
| 8,561,615 B2 | 10/2013 | Pannell et al. | |
| D886,297 S | 6/2020 | Van Wyk | |
| D903,867 S | 12/2020 | Van Wyk | |
| 11,291,493 B2 * | 4/2022 | Van Wyk | A61B 17/2812 |
| 11,291,581 B2 * | 4/2022 | Van Wyk | A61B 17/2816 |
| 11,723,680 B2 | 8/2023 | Van Wyk | |
| 11,844,540 B2 * | 12/2023 | Van Wyk | A61B 17/30 |
| 2001/0031961 A1 | 10/2001 | Hooven et al. | |
| 2002/0107517 A1 | 8/2002 | Witt et al. | |
| 2003/0069571 A1 | 4/2003 | Treat et al. | |
| 2003/0078577 A1 | 4/2003 | Truckai et al. | |
| 2004/0158286 A1 | 8/2004 | Roux et al. | |
| 2004/0249368 A1 | 12/2004 | Hooven | |
| 2005/0033353 A1 | 2/2005 | Jones | |
| 2005/0101952 A1 | 5/2005 | Lands et al. | |
| 2006/0069388 A1 | 3/2006 | Truckai et al. | |
| 2008/0077156 A1 | 3/2008 | Emstad | |
| 2008/0105265 A1 * | 5/2008 | Pannell | A61B 17/122 |
| | | | 606/45 |
| 2010/0145381 A1 | 6/2010 | Moon | |
| 2010/0288285 A1 | 11/2010 | Marmar | |
| 2013/0123819 A1 * | 5/2013 | Genau | A61B 17/00008 |
| | | | 606/159 |
| 2020/0170831 A1 | 1/2020 | Van Wyk | |

\* cited by examiner

METHOD FOR PERCUTANEOUS TREATMENT OF VESSELS

PRIORITY

The instant application claims the benefit of U.S. Provisional Application No. 63/475,193 filed Oct. 21, 2022, the contents of which are incorporated by reference herein.

The instant application is also a continuation-in-part of U.S. patent application Ser. No. 18/341,375 filed Jun. 26, 2023, which, in turn, is a continuation of U.S. patent application Ser. No. 17/709,675 filed Mar. 31, 2022 (now U.S. Pat. No. 11,723,680), which, in turn, is a continuation-in-part of U.S. patent application Ser. No. 16/700,393 filed Dec. 2, 2019 (now U.S. Pat. No. 11,291,581), which, in turn, claims the benefit of U.S. Provisional Application Ser. No. 62/917,325 filed Dec. 3, 2018.

U.S. patent application Ser. No. 17/709,675 filed Mar. 31, 2022 is also a continuation-in-part of U.S. Pat. No. 17,338,115 filed Jun. 3, 2021 (now U.S. Pat. No. 11,291,493), which, in turn, is a continuation-in-part of U.S. patent application Ser. No. 17/150,313 filed Jan. 15, 2021 (now abandoned), which, in turn, both claims the benefit of U.S. Provisional Application Ser. No. 62/995,188 filed Jan. 16, 2020 and is a continuation-in-part of U.S. patent application Ser. No. 16/700,393 filed Dec. 2, 2019 (now U.S. Pat. No. 11,291,581), which, as noted above, claims the benefit of U.S. Provisional Application Ser. No. 62/917,325 filed Dec. 3, 2018. The contents of all such prior applications are hereby incorporated by reference in their entirety.

TECHNICAL FIELD OF THE PRESENT INVENTION

The present invention relates generally to surgical instruments and methods for percutaneously, or through other surrounding tissue, sealing or otherwise occluding and dividing a vein, vessel, or other accessible duct of a patient. More particularly, the present invention relates to a percutaneous method, device, and system for treating conditions associated with bulging, swollen dilated, and/or raised vessels, for example, superficial thrombophlebitis, also known as "varicosed veins".

BACKGROUND OF THE PRESENT INVENTION

Varicose(d) veins occur when the walls of veins become weakened. This may be due to a variety of causes including hypertension, being overweight, restrictive clothing, or standing for extended periods of time, among others. As blood pressure in the vein increases, veins expand and may distort into twisted patterns as the vein length increases. This stretching of vein causes the valves in the vein to lose functionality. Failing valves cause sluggish blood to back up or pool in the vein, which, in turn, causes the vein to swell, bulge, twist and discolor.

While the condition of varicosity is largely chronic and incurable, available treatments can reduce the appearance of and relieve the discomfort associated with varicose veins. Examples of such conventional treatments include, but are not limited to, limb elevation (wherein legs are elevated above the waist multiple times a day to increase blood flow and decrease pressure in the veins) and compression techniques (wherein supportive stockings or socks compress the veins to prevent stretching, help blood flow, and reduce discomfort). In more severe cases, clinical interventions may be required to block the vein. In each case, the vein is blocked, becomes scar tissue, and is finally absorbed by the body.

For example, during injection therapy ("sclerotherapy"), a healthcare provider injects a solution into the vein that causes the vein walls to stick together. However, sclerotherapy has certain known side effects including:
  Redness or bruising for a few days where a needle went into the skin;
  Brown areas (for several months) on skin where the needle touched; and
  Lumps or hardness for a few months;

An alternative, minimally invasive treatment option is endovenous thermal ablation (also known as endovenous "laser therapy" and "radiofrequency therapy"), a procedure in which a long thin catheter is used to guide a laser or radiofrequency tool into position, generate heat, and permanently seal off the damaged vein. As compared to invasive varicose vein surgery, endovenous thermal ablation has several benefits compared to varicose vein surgery, including:
  Less pain;
  Fewer complications;
  Minimal scarring;
  Positive cosmetic results (usually equal to or better than surgery); and
  Shorter recovery (one can return to his/her normal routine sooner).

That being said, an invasive varicose vein surgery referred to as "ligation and stripping", wherein a surgeon ties off the affected vein (ligation) to stop blood from pooling and then removes (strips) the vein through several incisions to prevent varicose veins from reappearing, is often the patient's best or only option. This stands in contrast to endovenous thermal ablation wherein the varicose vessel is sealed off but not removed. Accordingly, whereas endovenous thermal ablation is associated with a small incision, a relatively short recovery time and fewer complications, varicose vein surgery requires significant surgical skill and several weeks of recovery, and complications often result.

Unfortunately, all the presently available therapies have significant drawbacks. For example, in the context of sclerotherapy, new varicose veins can happen and need treatment. Similarly, half of the patients who undergo surgical stripping get varicose veins again within five years. Likewise, varicose veins can recur after endovenous thermal ablation as well. In addition, both of these treatments have a significant potential for negative side effects including:
  Scarring;
  Skin burns;
  Infection;
  Injury to a nerve; and
  Deep vein thrombosis (a blood clot in a vein deep inside the body).

Accordingly, there is a need in the art for a varicose vein therapy that utilizes simplified instruments to occlude and divide the vein simply and quickly and with fewer steps and fewer post-surgical complications. To that end, the present invention addresses the ongoing need in the art for expeditious treatment methods that reduce scarring, burning and nerve injury, avoid the formation of hematomas and blood clots, minimize the potential for spontaneous regeneration and undesired resumption of varicosity, and negate the need for a highly skilled surgical professional, an extended procedure duration, and a prolonged recovery time. Furthermore, the present invention addresses the consistent preference in the art for methods that avoid the need for sharp instruments so that clinicians may limit their exposure to a patient's body fluids and thus operate on patients with infectious diseases such as HIV without risk of infection.

SUMMARY OF THE PRESENT INVENTION

The present invention addresses the afore-noted needs in the art by providing a novel and improved method occluding and dividing a vein, vessel, or other duct of a patient, more particularly a varicose vein, spider vein, or the like. Namely, using the bipolar coagulating devices and excising instruments described herein, a varicosity may be quickly and simply occluded, divided, and separated by fascial interposition. For example, in the methods of the present invention, a varicose vein or other duct or vessel in need of treatment is isolated within a fold of skin or other surrounding tissue portion using a non-conductive clamp and clamped between the jaws of a bipolar coagulating device. Using RF energy, the portion of the fold of skin or other surrounding tissue portion and the vessel positioned therein that is clamped between the jaws is fused by coagulation so as to occlude the vessel in two places. Thereafter the clamp and handpiece jaws are removed from the site. Coagulation of the tissue prevents blood flow to the central uncoagulated region. Because of this, tissue in this region will necrose and slough from the body so as to divide the vessel. Optionally, the center portion of uncoagulated tissue in the center of the coagulated region may be excised using the original clamp or another suitable instrument.

It is therefore an objective of the present invention to provide a method for occluding and dividing a vein, vessel, or duct in need thereof that includes the steps of:
(a) locating a bulging, swollen, raised or dilated length of said vein, vessel, or duct;
(b) positioning a surgical clamp about the vein, vessel, or duct so as to temporarily isolate the length;
(c) providing a coagulating bipolar device having a proximal handle portion that defines a longitudinal axis of said device and an active distal portion characterized by a pair of oppositely-faced, upper and lower coagulating jaws, wherein each of said jaws is (i) movable between open and closed positions, and (ii) provided with mating distal tips and inner edges, whereby, when said jaws are in the closed position and viewed in a plan view, said mating inner edges engage to define an interior perimeter comprised of (1) an open central slot that terminates in (2) lateral opening sized to permit said distal clamping portion to be positioned around said tissue-capturing distal portion of said surgical clamp that retains said tissue-capturing distal end of said surgical clamp that retains said length of vein, vessel, or duct located in step (a) and isolated in step (b);
(d) tightly closing the jaws about the tissue-capturing distal portion of the surgical clamp to thereby define a first area of clamped tissue disposed between the closed jaws and a second area defined by the interior perimeter that includes the isolated length of vein, vessel or duct retained by the tissue-capturing distal portion of the surgical clamp; and
(e) activating the coagulating bipolar device so as to coagulate the first area of clamped tissue.

In a preferred embodiment, the inventive method may optionally further include step (f), wherein both the coagulating device and surgical clamp are disengaged from the vein, vessel, or duct.

In certain preferred embodiments, the method may further include the step of sliding the tissue-capturing distal end of the surgical clamp relative to the jaws of the bipolar device in a direction normal to a plane defined by the coagulating jaws, whereby outer surfaces perimetral to the tissue-capturing distal end of the surgical clamp interact with the mating inner edges of the coagulating jaws of said bipolar device so as to excise some or all of the second area, including the isolated length of vein, vessel, or duct, to thereby divide the first area of clamped tissue into two coagulated and sealed proximal and distal ends.

In an alternative embodiment, the mating inner edges of the upper and lower coagulating jaws may include planar cutting edges and the outer edge surfaces perimetral to the tissue-capturing distal end of the surgical clamp may include curvilinear sharpened surfaces, whereby the excision of some or all of the second area of the vein tissue, including the isolated length of vein, is achieved through shearing action that arises from engagement of said sharpened curvilinear surface with said planar cutting edges.

It is a further objective of the present invention to apply the above-recited method steps to the treatment of varicose (d) veins. In a particularly preferred embodiment, a bulging, swollen, raised, or dilated length of a varicosed vein may be percutaneously manipulated into a surface fold of the patient's skin. In the context of this embodiment, the vein may be a superficial tributary vein, a spider vein, or thread vein.

In a preferred embodiment, the above methods may optionally further include the step of percutaneously manipulating the length of the vein, vessel, or duct into a fold of adjacent dermal tissue, particularly when the vein at issue is a varicosed tributary vein or spider vein.

In a preferred embodiment, the surgical clamp utilized in the above methods may be a ring forceps or a tenaculum.

In a preferred embodiment, the upper and lower jaws as well as the first area of clamped tissue are arcuate in shape (e.g., comprising mirror-image "U-shaped" curves) such that the second area may include a convex region. In addition, the inner edges of the pair of oppositely-faced, upper and lower coagulating jaws may be optionally sharpened so as to enable direct excision of the second area that includes the isolated portion of the vein, vessel, or duct.

In a preferred embodiment, the coagulation of the first area of clamped tissue serves to occlude and divide the vein, vessel, or duct into separated sealed proximal and distal legs and, optionally, to deaden sensory nerves proximate to said first area of clamped tissue.

In a preferred embodiment, the mating distal tips are offset from the longitudinal axis of the device by about 30 to about 60 degrees, more preferably from about 40 to about 50 degrees.

These and other objectives can be accomplished by the invention herein disclosed. Further objects and features of the invention will become more fully apparent when the following detailed description is read in conjunction with the accompanying figures and examples. To that end, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not construed as limiting of the invention. For example, while methods of the present invention are described with regard to the treatment of varicose veins, the method may be used for the treatment of any subcutaneous condition requiring occlusion and dividing of veins and other ducts. All fall within the scope of this invention.

In addition, regarding the specific objectives recited above, it will be understood by those skilled in the art that one or more aspects of this invention can meet certain objectives, while one or more other aspects can meet certain other objectives. Each objective may not apply equally, in all its respects, to every aspect of this invention. As such, the objectives herein can be viewed in the alternative with respect to any one aspect of this invention.

BRIEF DESCRIPTION OF THE FIGURES

Various aspects and applications of the present invention will become apparent to the skilled artisan upon consideration of the brief description of figures and the detailed description of the present invention and its preferred embodiments that follows.

DETAILED DESCRIPTION OF PREFERRED EMBODIMENTS

Figure 1:
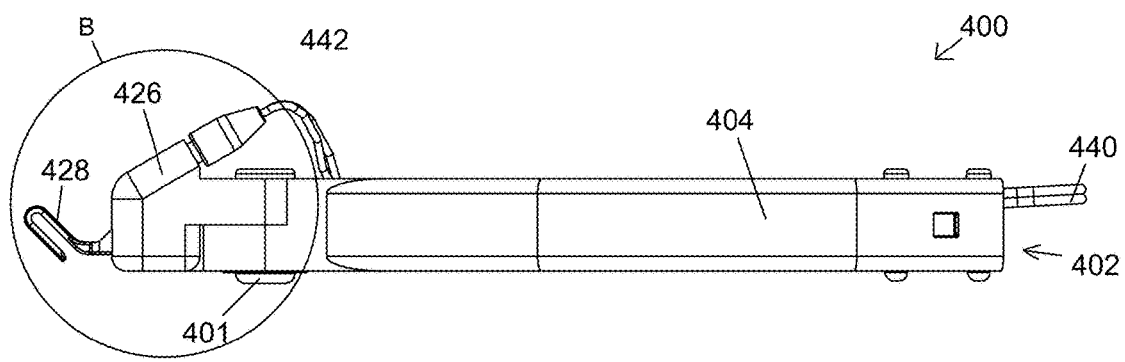
FIG. 1 is a plan view of a bipolar electrosurgical device of suitable for use in connection with the methods of the present invention.
Figure 2:
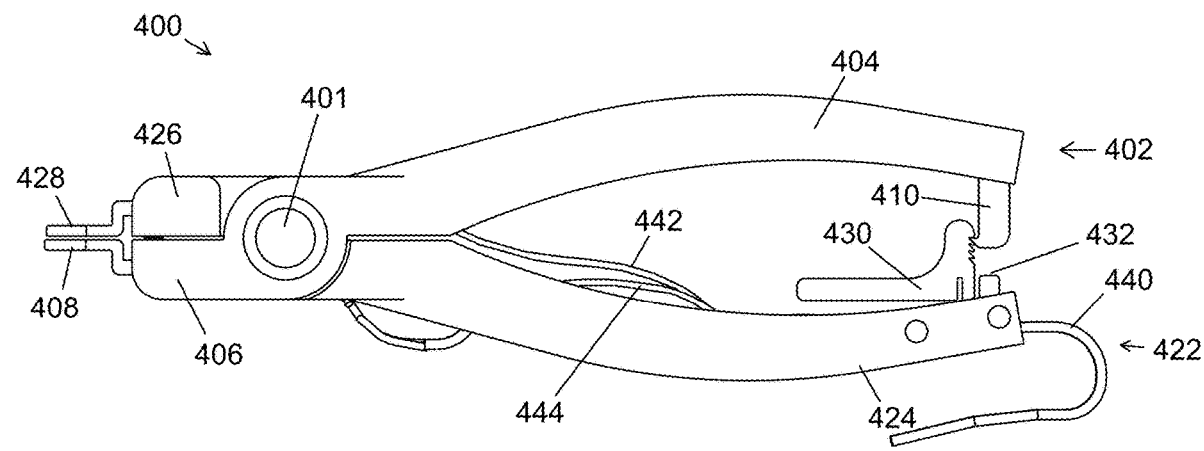
FIG. 2 is a side elevational view of the objects of FIG. 1.
Figure 3:
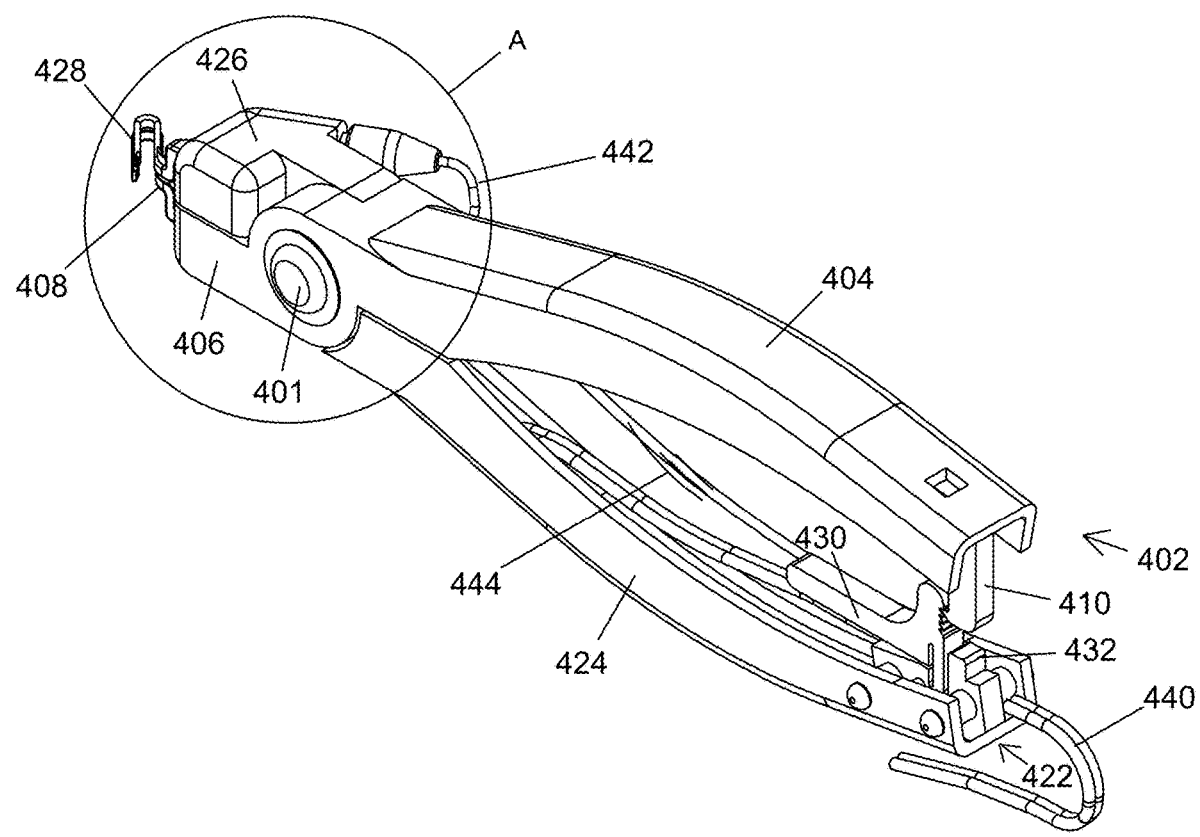
FIG. 3 is a perspective view of the objects of FIG. 1.

Before the present materials and methods are described, it is to be understood that this invention is not limited to the specific devices, systems, methodologies, or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

The words "a", "an", and "the" as used herein mean "at least one" unless otherwise specifically indicated. Thus, for example, reference to an "opening" is a reference to one or more openings and equivalents thereof known to those skilled in the art, and so forth.

As used herein, the noted directional terms relate to a human body in a standing position. For instance, "up" refers to the direction of the head, "down" refers to the direction of the feet. Likewise, herein, the "vertical" direction is parallel to the axis of the body and the "horizontal" direction is parallel to the floor. In a similar fashion, the term "lateral" refers to the direction extending away from the center of the body whereas "medial" refers to a direction extending toward the center of the body.

In the context of the present invention, the term "proximal" refers to that end or portion of a device or instrument which is situated closest to the body of the subject when the device is in use. Accordingly, the proximal end of an excising clamp or bipolar electrosurgical device of the present invention includes the handle portions.

In the context of the present invention, the term "distal" refers to that end or portion of a device or instrument that is situated farthest away from the body of the subject when the device is in use. Accordingly, the distal end of an excising clamp of the present invention includes the jaw components.

In the context of the present invention, the term "arcuate" is used herein to describe shapes forming or resembling an arch. It is used interchangeably with its synonym, arciform.

Reference may be made herein to "an arcuate sealed area" that contains one or more portions of the bulging, raised or dilated vessel, such as a varicosed vein. This "arcuate" area is exemplary only and not meant to be limiting. The sealed area may have a variety of regular or irregular shapes. Any sealed area formed by bipolar jaws positioned distal to a clamp located on swollen portion of the vessel falls within the scope of this invention. As such, the sealed region may be arcuate, linear, irregularly shaped, or a combination of linear and curvilinear segments.

In the context of present invention reference invention, the terms "coagulated" or "cauterized" are interchangeably used to describe a treated area of tissue. As used herein, coagulated or cauterized tissue is tissue that through the application of RF energy and pressure has been desiccated and fused to eliminate the flow of blood or other fluids.

In the context of the present invention, the term "convex" refers to a surface or boundary that curves outward, as the exterior of a sphere. Conversely, the term "concave" refers to a surface or boundary that curves inward, as to the inner surface of a sphere, or is hollowed or rounded inward like the inside of a bowl. Herein, the area of unclamped tissue defined by the U-shaped jaws of the bipolar coagulating device and the arcuate area of clamped scrotal tissue contained therein is referred to as convex in shape.

The present invention makes reference to percutaneously sealing and/or occluding and dividing a "vein, vessel or other duct" of a patient. In the biological context of the present invention, the term "vessel" refers to a tube or canal in the body (such as an artery, vein, or lymphatic vessel) in which a body fluid (such as blood or lymph) is contained and conveyed or circulated. Similarly, the term "duct" refers herein to a bodily tube or vessel, particularly one that carries the secretion of a gland. The term "vein" refers to a particular subset of blood vessels, namely any of the tubular branching vessels that carry blood from the capillaries toward the heart.

In the medical context, such as in the present invention, the terms "varicose" and "varicosed" are used interchangeably to mean abnormally swollen or dilated. Accordingly, in the context of the present invention, the terms "varicose(d) veins" and "superficial thrombophlebitis" are used interchangeably to refer to the condition wherein blood vessels that lie just under the skin, e.g., superficial tributary veins, become twisted and swollen. As discussed above, varicose (d) veins, or "varicosities", are caused by an increase in blood pressure in the veins that can arise from a number of underlying conditions, from hypertension to obesity to pregnancy. Increased pressure leads to a weakening in the vessel wall or the one-way valves that move blood towards the heart that, in turn, causes the vessels to dilate and enlarge. When the valves or vessel walls become weakened or damaged, blood can collect in the veins and form "varicosities". The condition occurs most frequently in the legs, with the raised veins being easily visible through the skin.

While varicose veins are only an aesthetic concern in some patients, for others they give rise to localized symptoms such as pain, limb heaviness, cramping, burning, swelling or itchiness that can be an indication of more serious health problems. Other symptoms include aching, heavy and uncomfortable legs, swollen feet and ankles, muscle cramps in the legs, and dry skin and color changes in the lower leg.

In the context of the present invention, the terms "spider veins" and "thread veins" are used interchangeably to refer to small, damaged veins, usually blue, red, or purple in color, that appear on the legs or face as thin lines or branched webs. Spider veins arise in capillaries close to the surface and thus tend to be easily visible through the skin. As with varicose veins, spider veins stem from malfunctioning valves in blood vessels: the blood moving through the vein does not move forward properly, causing an enlarged vein. However, where varicose veins are raised, swollen blood vessels that twist and turn beneath the skin, spider veins are smaller, more superficial blood vessels. Additionally, whereas varicose veins can be very painful, spider veins do not often cause pain or indicate worsening health conditions but rather are treated for purely cosmetic reasons.

The instant invention makes reference to certain surgical instruments that are configured both for clamping tissue or capturing a vessel, vein, or duct and for excision of clamped or captured tissue. The present invention additionally makes reference to instruments, often referred to herein as "excising" or "excision" clamps or hooks, designed for use in conjunction with such bipolar coagulating devices to facilitate the methods of the present invention, namely, to position a vessel, such as a varicosed vein, within the jaws of the bipolar coagulating device, to maintain that position during coagulation, and thereafter to optionally divide the vessel by excision. Of particular interest are the bipolar coagulating devices and associated clamps and hooks described in U.S. Utility Pat. Nos. 11,723,680, 11,291,581, and 11,291,493, U.S. Design Patent Nos. D9038675, D8862975, and D9500555, and U.S. Patent Publication No. 2023/0329736 A1, the contents of which are hereby incorporated by reference in their entirety.

Clamping devices in varicose vein treatment methods of the present invention are used solely to maintain the position of a vessel in a fold of skin or surrounding tissue for subsequent occlusion of the vessel. Because a clamping device may contact the jaws of a bipolar handpiece during use, in order to prevent shorting of the bipolar device these clamps are formed of a dielectric material, typically a polymer or ceramic, or are formed of a metallic material and are covered with a dielectric coating. Indeed, clamps having a wide variety of configurations may be used including a standard metal ring forceps and tenaculum to which a non-conductive coating has been applied.

As noted above, the present invention is characterized by substantial advantages not found in conventional methods and devices. For example, in the context of the present invention, nerves in the sealed region and closely adjacent thereto are destroyed or deadened by a process known as RF neurotomy so as to reduce the probability of post procedure pain. In addition, in those embodiments that avoid direct dissection and resulting bleeding, the present invention is able to eliminate the risk for development of massive hematomas and swelling and thereby reduce the risk of blood clots, a common complication of varicose vein surgery. In addition, the present invention allows for the separation of a vessel in such a manner that it is virtually impossible for the sealed ends of the vessel to contact each other and rejoin, reform, and/or recur. In addition, the vessel dissection procedure of the present invention, particularly as applied to varicose vein therapy, requires fewer steps than that of currently available techniques, thereby reducing opportunities for complications and medical errors. Furthermore, the inherent simplicity of the disclosed procedure and associated instruments simplifies training and allows clinicians with limited experience to master their use. Moreover, the procedures of the present invention reduce exposure to bodily fluids, which, in turn, reduces the risks of transmission of blood-borne diseases, such a HIV and Hepatitis, to performing clinicians.

Although methods and materials similar or equivalent to those described herein can be used in the practice or testing of embodiments of the present invention, the preferred methods, devices, and materials are depicted in the accompanying figures and described hereinafter. However, the embodiments described herein are merely intended to illustrate the principles of the invention. Those skilled in the art will recognize that variations and modifications may be made to the embodiments without changing the principles of the invention herein disclosed. Accordingly, the accompanying figures, described in detail below that depict aspects of the invention are in no way intended to limit the scope of the present invention.

EXAMPLES

Methods of the present invention are now described with reference to the occlusion of a varicose vein. However, it will be understood that methods of the present invention may be used to treat any bulging, swollen, raised or dilated vessel without removal of the vessel from the surrounding tissue in which it is encased.

In an exemplary embodiment herein described, the vessel is a varicose vein. In methods of the present invention, a varicose vein in need of treatment is located percutaneously and manipulated into a fold of skin. The position of the vein in the fold is maintained using a clamp, the clamp being positioned just distal to the vein. Thereafter, the jaws of a bipolar coagulating device are positioned around the clamp and closed onto the tissue so as to compress a region of tissue surrounding the clamp. Radio Frequency (RF) energy from the bipolar outputs of an electrosurgical generator is applied to the jaws so as to coagulate the tissue compressed between the jaws of the handpiece. This seals the two vein portions clamped between the jaws along with dermal tissue clamped between the jaws. A small region of dermal tissue and a third vein portion between the two sealed portions remains uncoagulated. When coagulation is finished the handpiece and clamp are removed from the site to complete the procedure. The vein is now occluded in two locations with an uncoagulated portion between the occlusion sites. The uncoagulated tissue need not be immediately removed during the procedure. Because the coagulation has blocked the blood supply to this tissue, it will necrose and slough off naturally over time thereby dividing the vein. However, in certain instances, the practitioner may elect to actively excise the intervening tissue.

Referring now to the accompanying figures, a bipolar coagulating device (handpiece) 400 used in methods of the present invention is depicted in FIGS. 1 through 6 with the jaws in a first, closed or clamped position. Handpiece 400 is substantially similar to the equivalent electrosurgical device described in U.S. Pat. Nos. 8,220,464 and 8,561,615 and analogous to the coagulating bipolar devices described U.S. Pat. Nos. 11,723,680, 11,291,581, and 11,291,493, the contents of which are hereby incorporated by reference in their entirety. As such, the device operates by an analogous method. To wit, bipolar handpiece 400 has an upper handle assembly 402 with a proximal handle portion 404 and a distal portion 406 wherein is mounted lower jaw 408. Handpiece 400 has a lower handle assembly 422 with a proximal handle portion 424 and a distal portion 426 wherein is mounted upper jaw 428. Upper handle assembly 402 and lower handle assembly 422 are rotatably joined by element 401. Lower handle assembly 422 has located adjacent to its proximal end ratchet element 430 that, in cooperation with downward extending proximal portion 410 of upper handle assembly 402 maintains the clamping force of jaws 408 and 428, portion 432 of ratchet element 430 limiting the inter-jaw force that can be applied. Bipolar cable 440 is connected at its proximal end to the bipolar outputs of a suitable electrosurgical generator, and at its distal end, via wires 442 and 444 to upper jaw 428 and lower jaw 408, respectively, such that Radio Frequency (RF) energy from the generator is conducted to jaws 408 and 428 so as to coagulate tissue clamped therebetween. In a preferred embodiment, RF energy from the electrosurgical generator is modulated according to an algorithm in the generator for maximal coagulation of tissue between the jaws.

Figure 4:
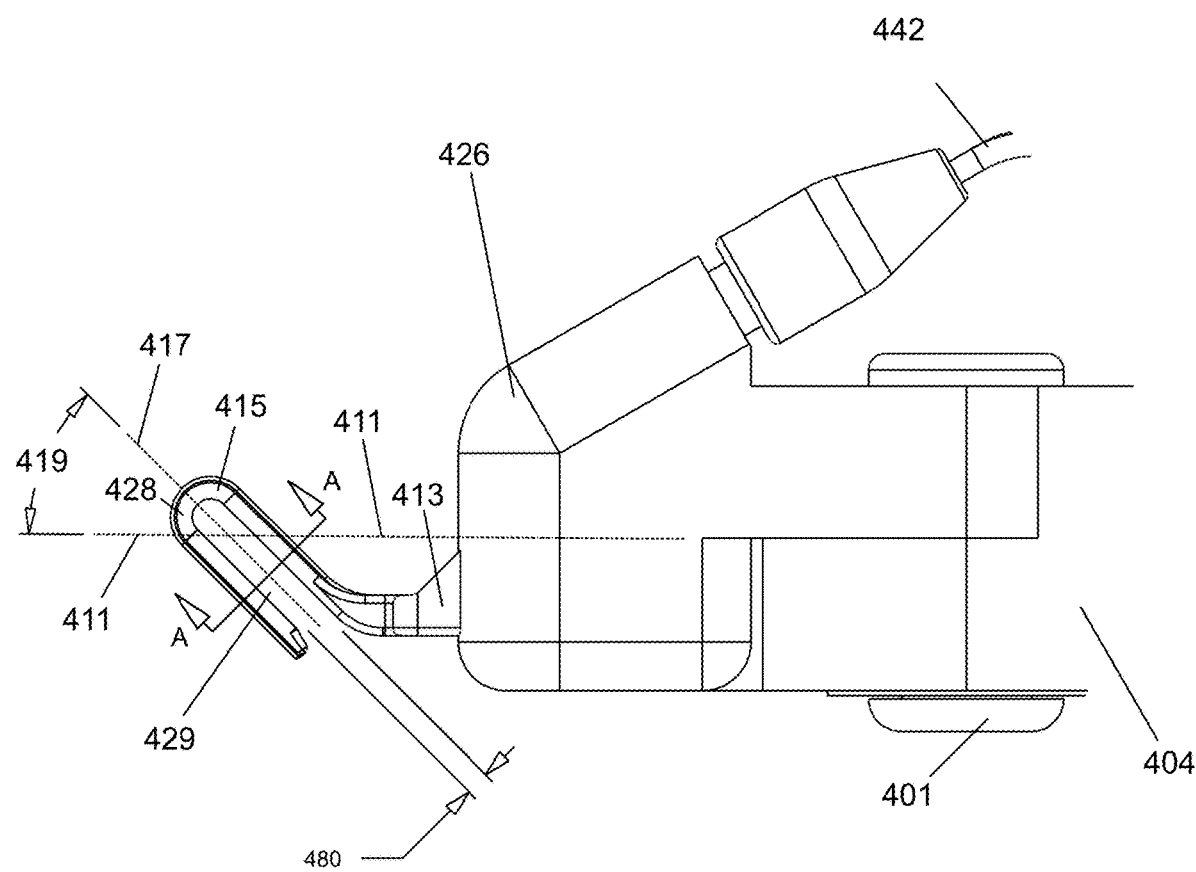
FIG. 4 is an expanded view of the objects of FIG. 1 at location B.
Figure 5:
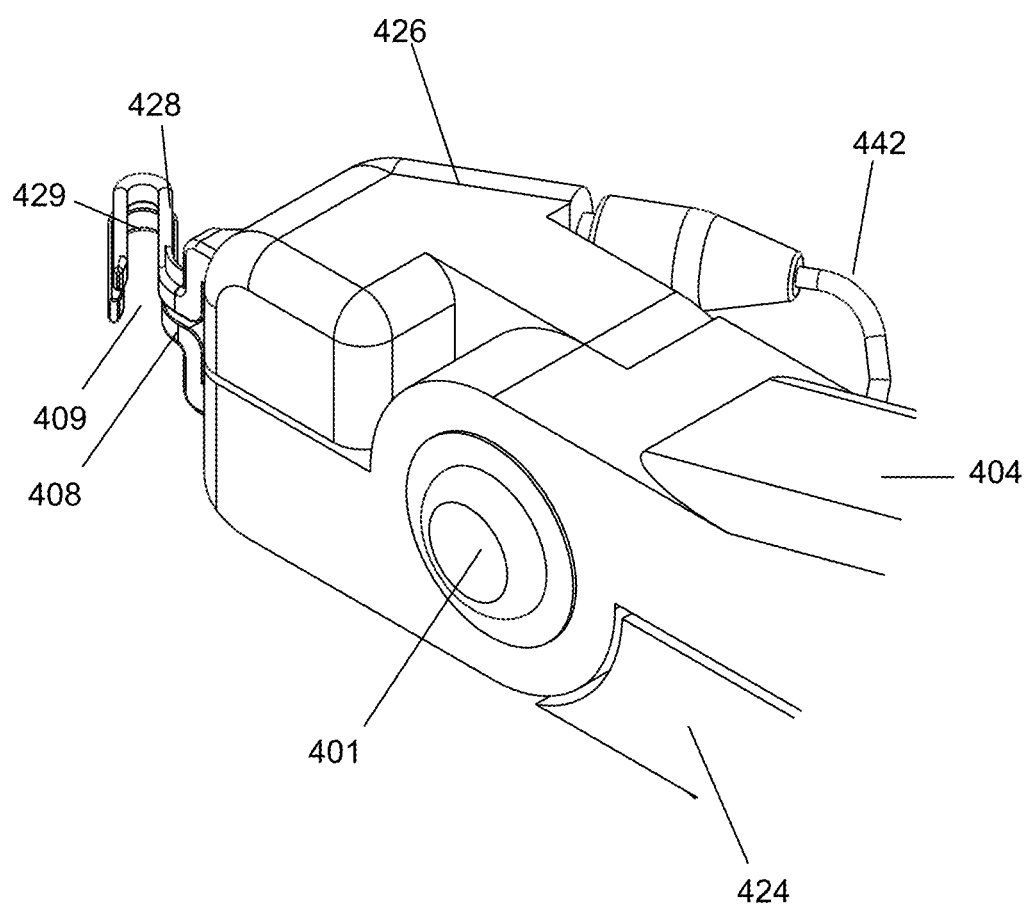
FIG. 5 is an expanded view of the objects of FIG. 3 at location A.
Figure 6:
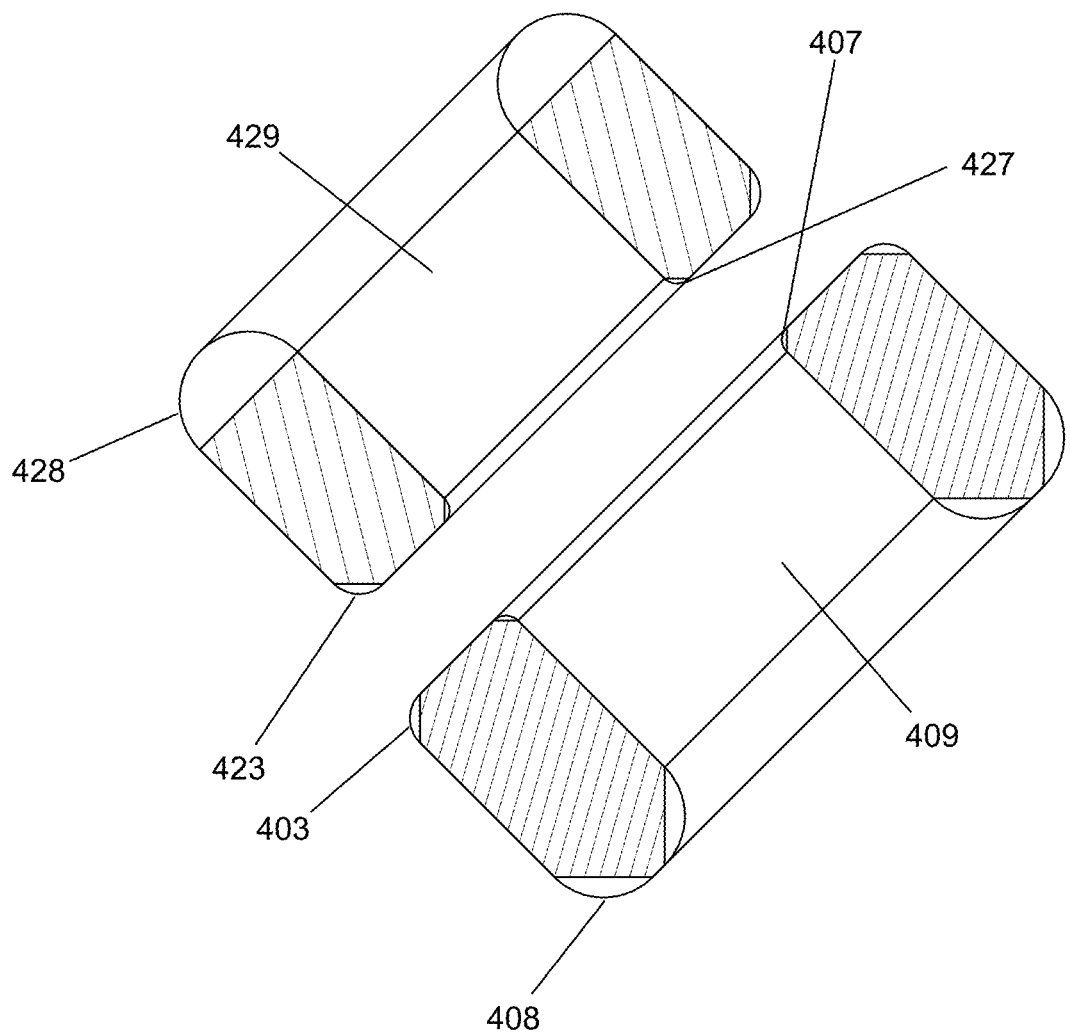
FIG. 6 is an expanded sectional view of the objects of FIG. 4 at location A-A.

As best seen in the expanded view of FIGS. 4, 5 and 6, upper 428 and lower 408 jaws are mirror images, each including a proximal portion 413 that attaches to the distal end of the handpiece and a distal portion 415 that is off-set from the longitudinal axis 411 defined by the handpiece, preferably disposed at an angle 419 of about 45 degrees from the centerline 417 of slot 429. The angular offset affords the surgeon better visibility and access to the target surgical site. As best seen in FIG. 4, upper jaw 428 has a "U" shape with a central slot 429 of width 480, with lower jaw 408 having a corresponding shape so that tissue may be clamped between the U-shaped jaw portions of jaws 408 and 428.

Referring now to FIG. 6, the U-portions of jaws 408 and 428 have radiused outer circumferential portions 403 and 423, respectively, adjacent to their clamping surfaces to prevent cutting of tissue clamped between jaws 408 and 428. In a preferred embodiment, each offset central slot defined by each "U-shaped" distal portion is approximately 1-3 mm in width. Jaws 408 and 428 are preferably formed of a stainless steel or other suitable metallic material.

Figure 7:
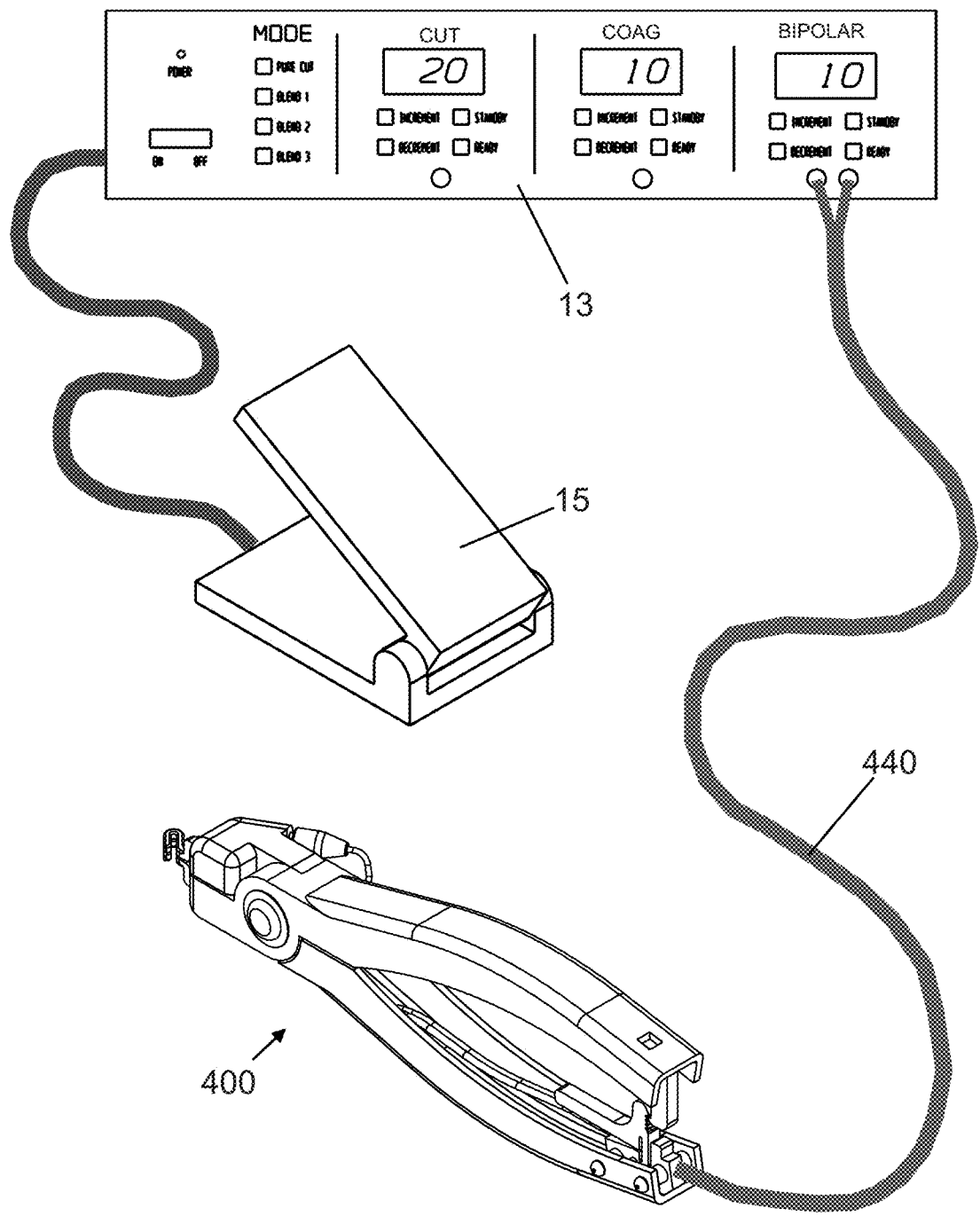
FIG. 7 depicts a surgical system including the bipolar electrosurgical device of FIG. 1 connected to a suitable electrosurgical generator with optional foot pedal connected thereto for activation of the generator.
Figure 8:
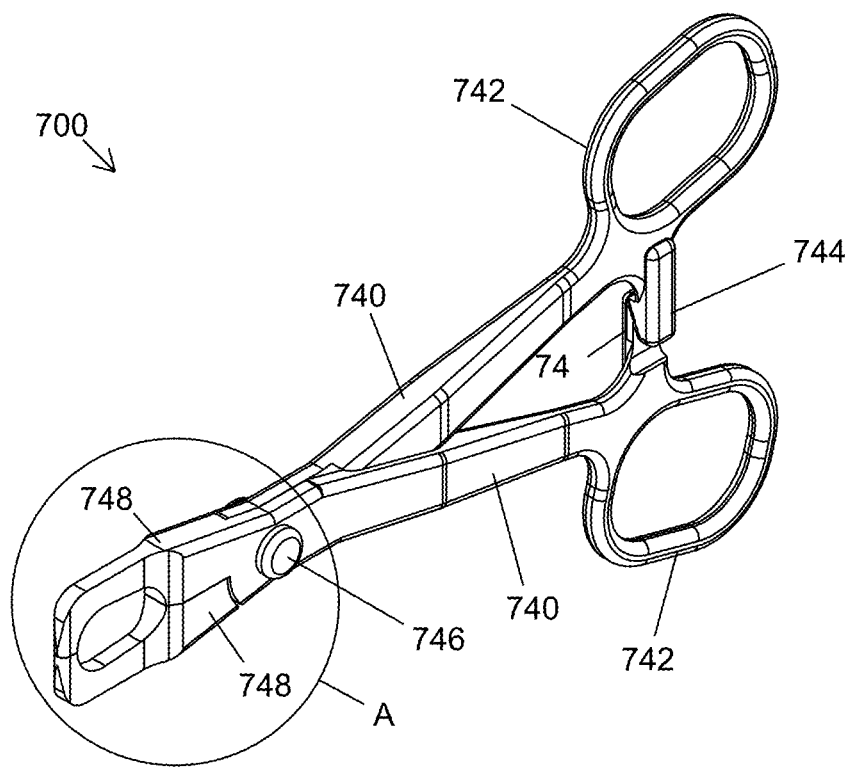
FIG. 8 is a perspective view of an isolating clamp in accordance with the present invention in a closed (clamped) condition.
Figure 9:
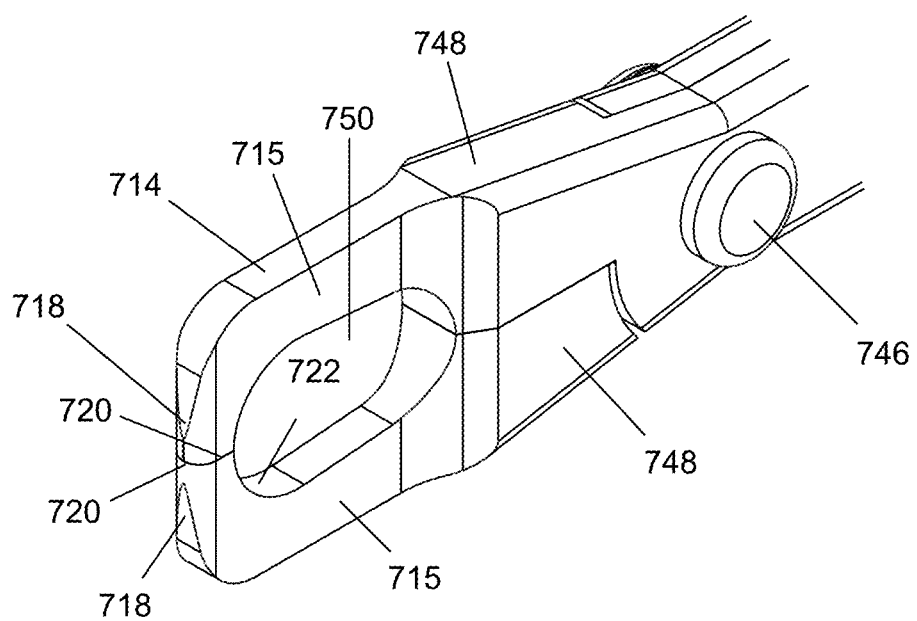
FIG. 9 is an expanded view of the objects of FIG. 8 at location A.
Figure 10:
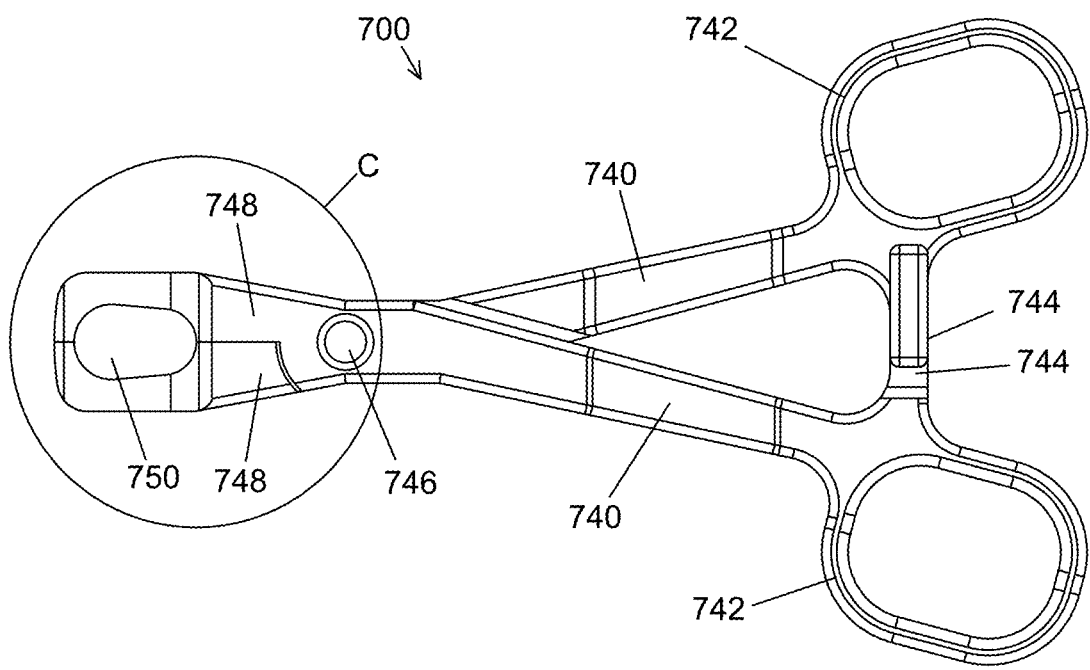
FIG. 10 is a side elevational view of the objects of FIG. 19.
Figure 11:
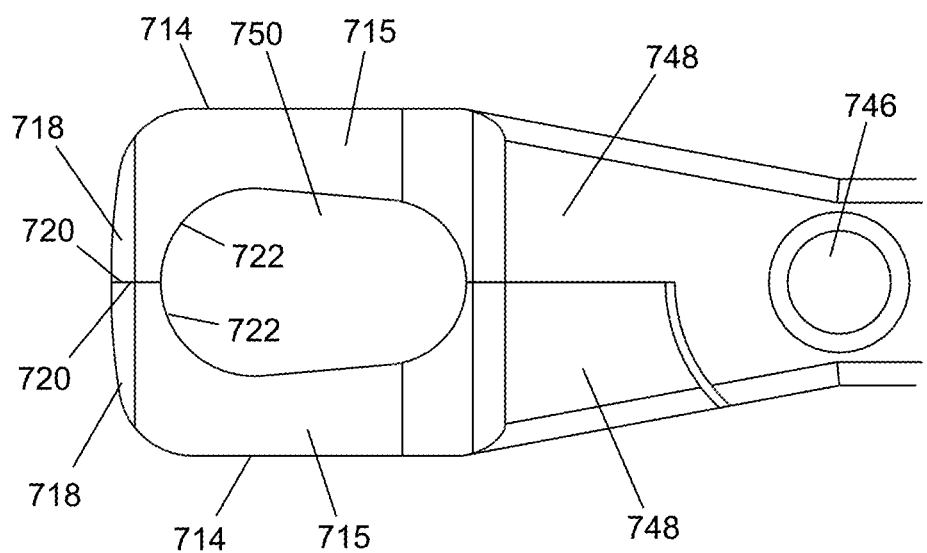
FIG. 11 is an expanded view of the objects of FIG. 10 at location C.
Figure 12:
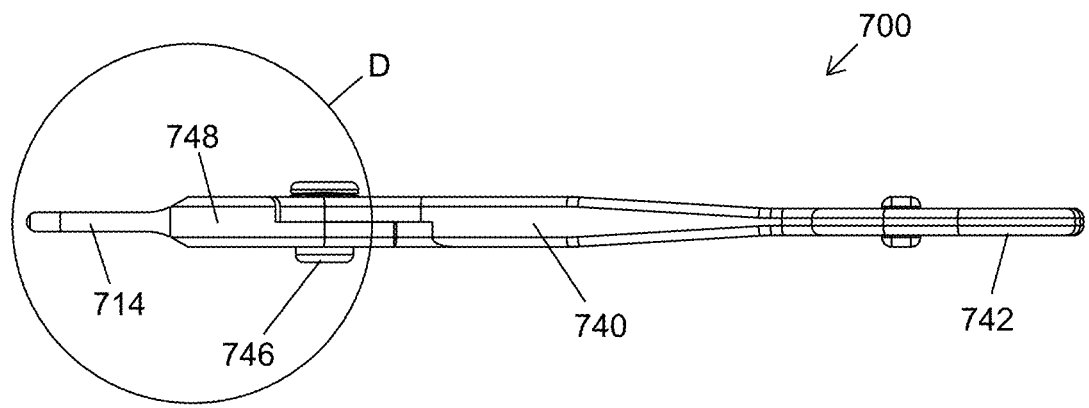
FIG. 12 is a plan view of the objects of FIG. 8.
Figure 13:
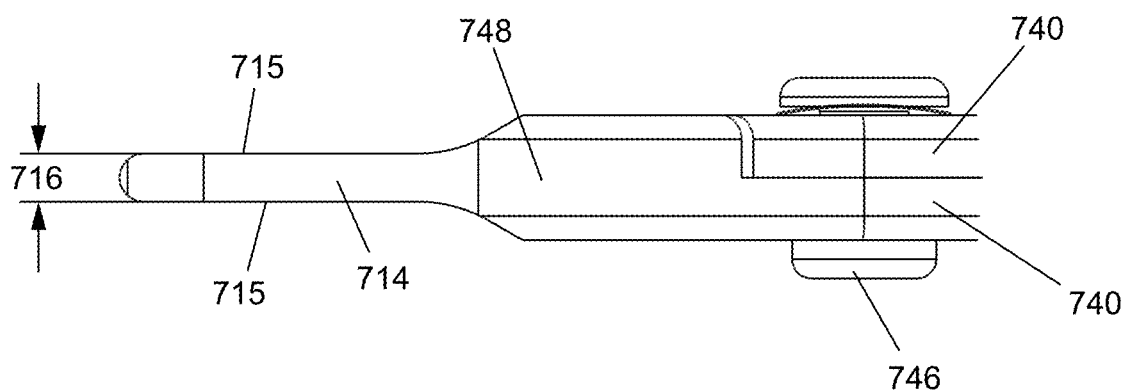
FIG. 13 is an expanded view of the objects of FIG. 12 at location D.
Figure 14:
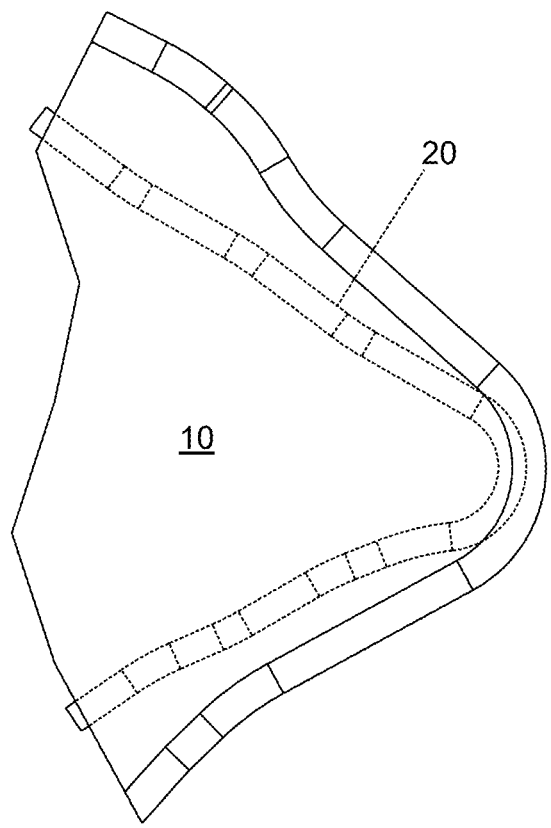
FIG. 14 is a plan view of a portion of skin with a varicose vein in need of treatment positioned in a fold thereof.
Figure 15:
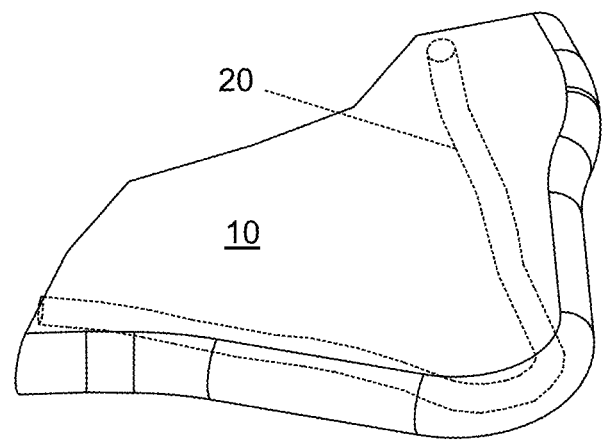
FIG. 15 is a perspective view of the objects of FIG. 14.

FIG. 7 depicts bipolar coagulating device 400 connected by cable 440 to the bipolar outputs of electrosurgical generator 13 for use in connection with the methods of the present invention. In the depicted preferred embodiment, generator 13 is activated by foot pedal 15.

In FIGS. 8 through 13, clamp 700 is formed of elements 740 having proximal portions that form finger holes 742, and whereon are formed mating ratchet portions 744. Elements 740 are pivotably joined by element 746. Distal to element 746, distal portions 748 of elements 740 have a distal-most portion 714 of width 716 (FIG. 13) that is less than width 480 of slots 429 and 409 of jaws 428 and 408 respectively (see FIG. 5). Distal-most portions 714 have at their distal ends jaw portions 718 with vertically opposed, planar jaw faces 720. Distal-most portions 714 have laterally opposed surfaces 715, and surfaces 722 that are perpendicular to surfaces 715, and that together define distal opening 750 of clamp 700. Clamp 700 may be made from a suitable dielectric material or from a metallic material with the distal portions 714 coated with a suitable dielectric coating so as to prevent shorting of bipolar handpiece 400 during use.

Figure 16:
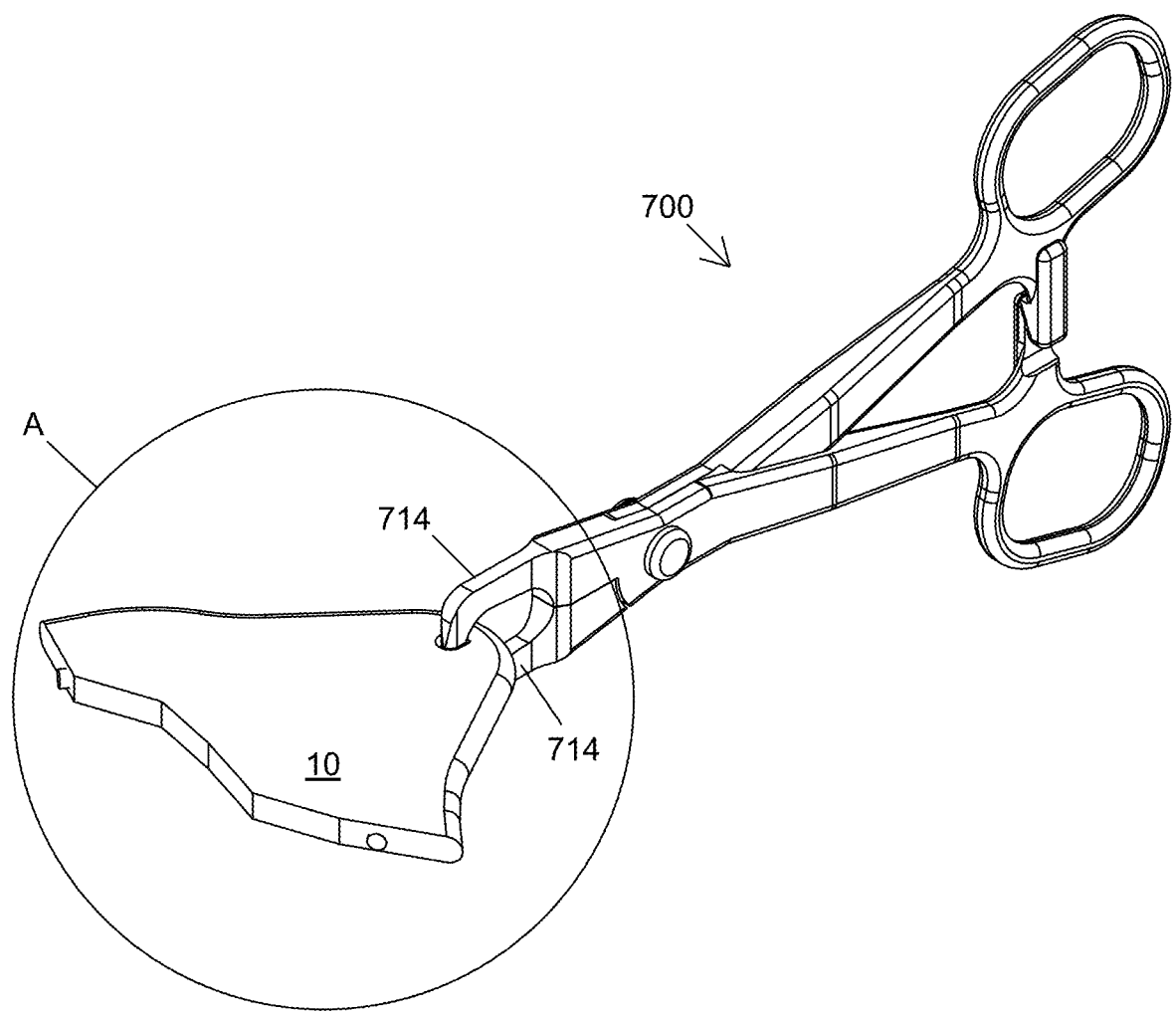
FIG. 16 depicts the skin of FIG. 14 wherein the position of the vein is maintained by the isolating clamp of FIG. 8.
Figure 17:
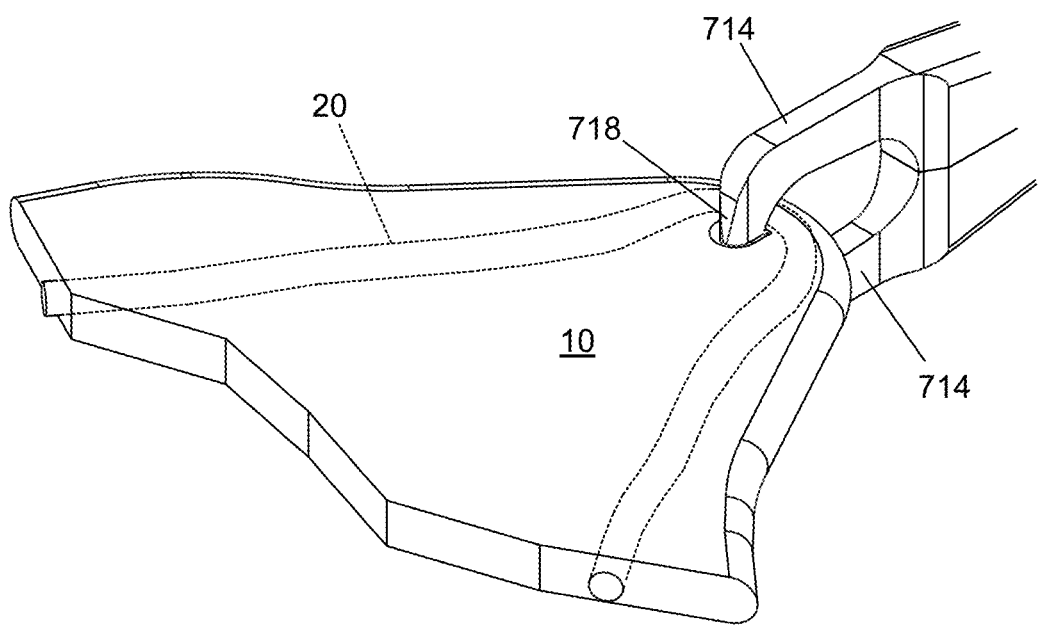
FIG. 17 is an expanded view of the objects of FIG. 16 at location A.
Figure 18:
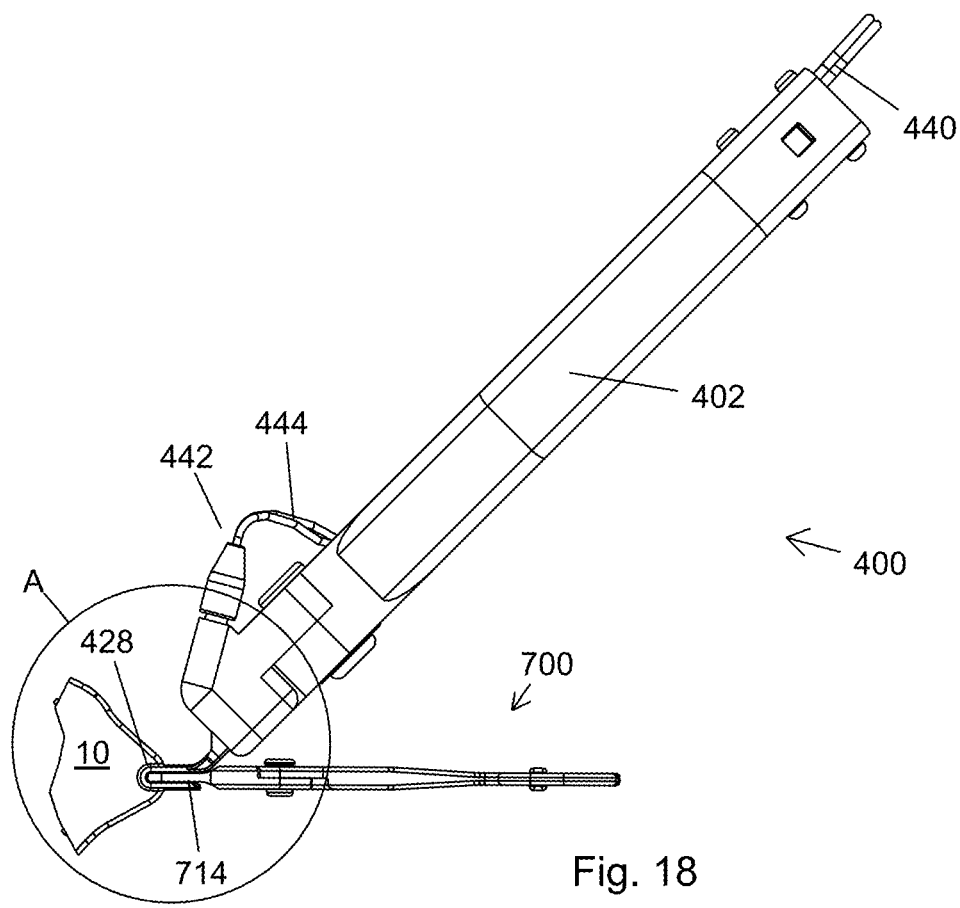
FIG. 18 is a plan view of the skin and clamp of FIG. 16 wherein the jaws of the bipolar handpiece of FIG. 1 are positioned around the clamp in preparation of sealing the tissue between the jaws by coagulation.
Figure 19:
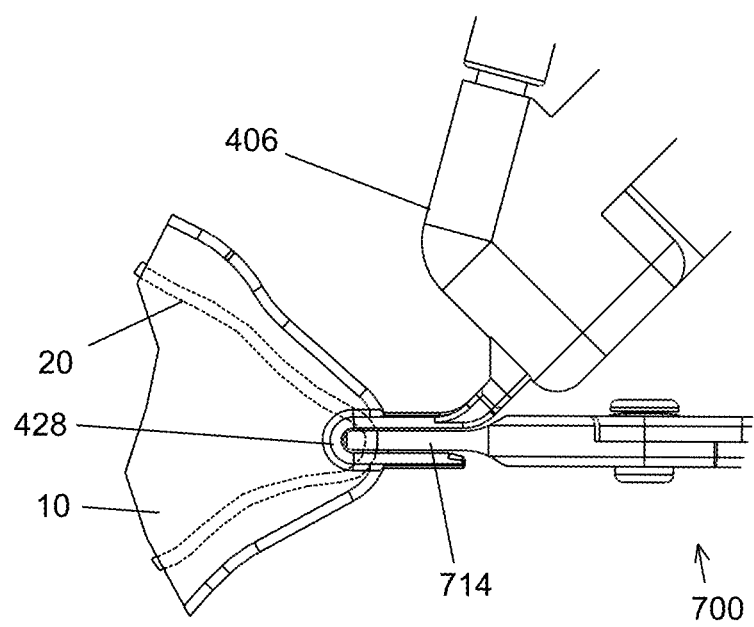
FIG. 19 is an expanded view of the objects of FIG. 18 at location A.
Figure 20:
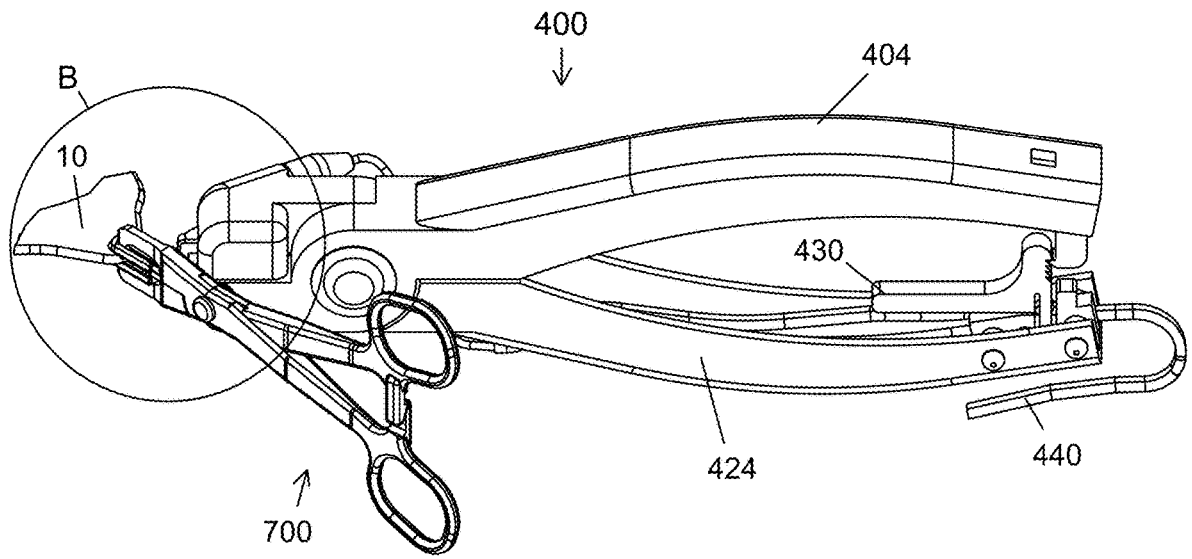
FIG. 20 is a perspective view of the objects of FIG. 18.
Figure 21:
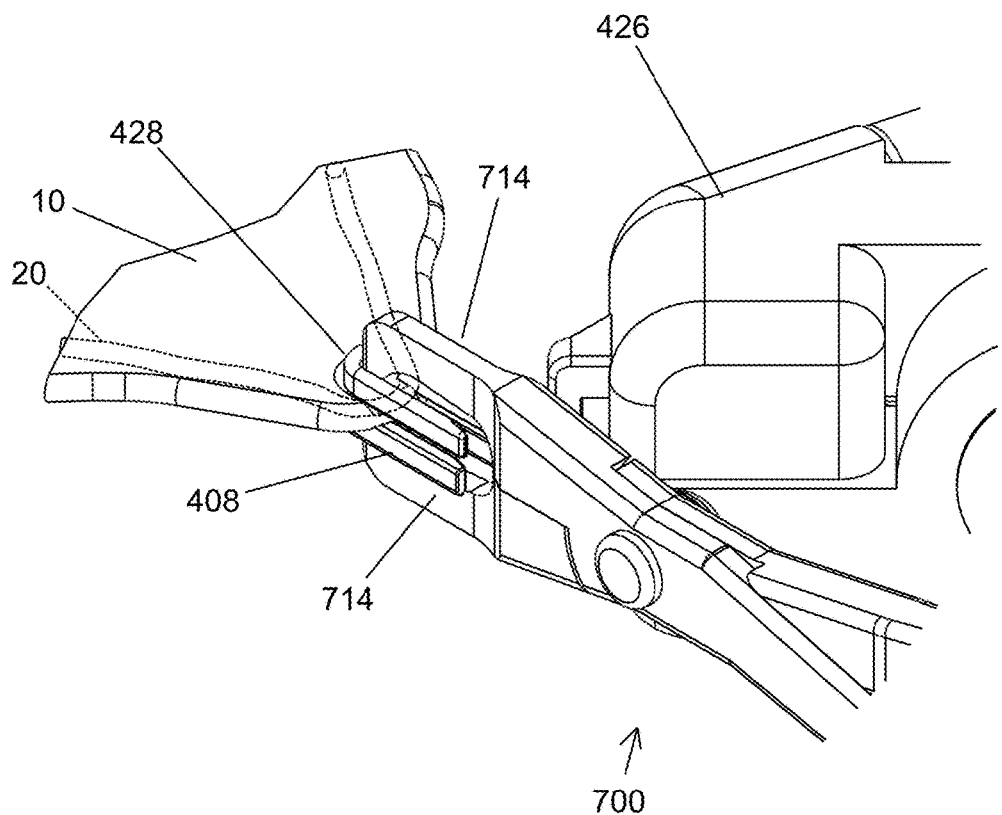
FIG. 21 is an expanded view of the objects of FIG. 20 at location A.
Figure 22:
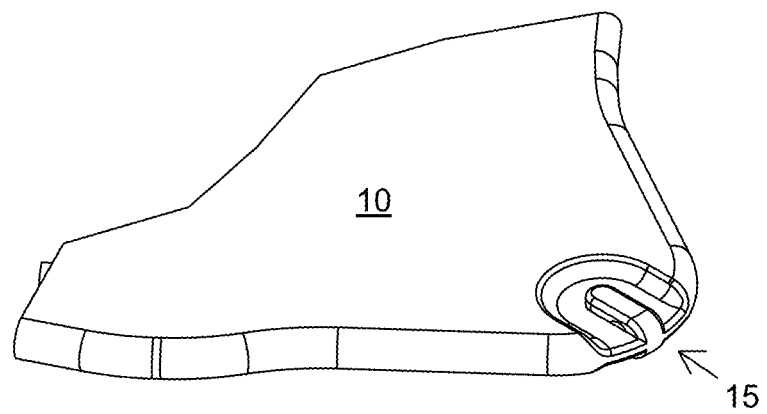
FIG. 22 is a perspective depiction of a skin portion wherein a varicose vein in heed of treatment has been divided and occluded according to methods of the present invention.
Figure 23:
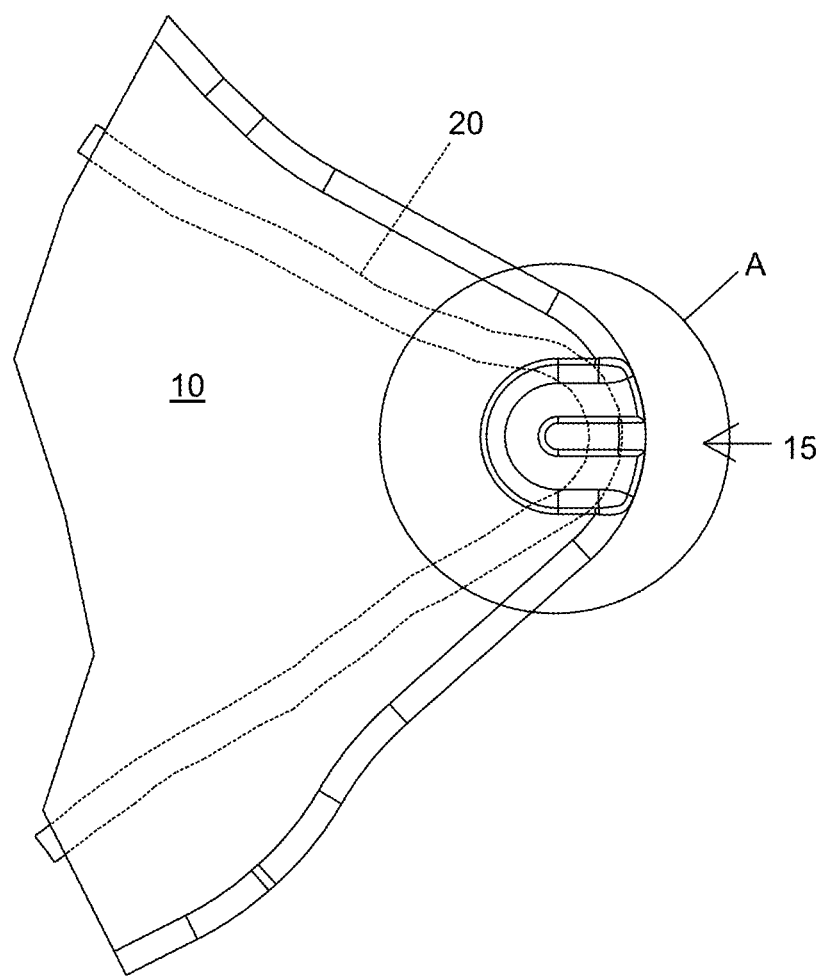
FIG. 23 is a plan view of the objects of FIG. 22.
Figure 24:
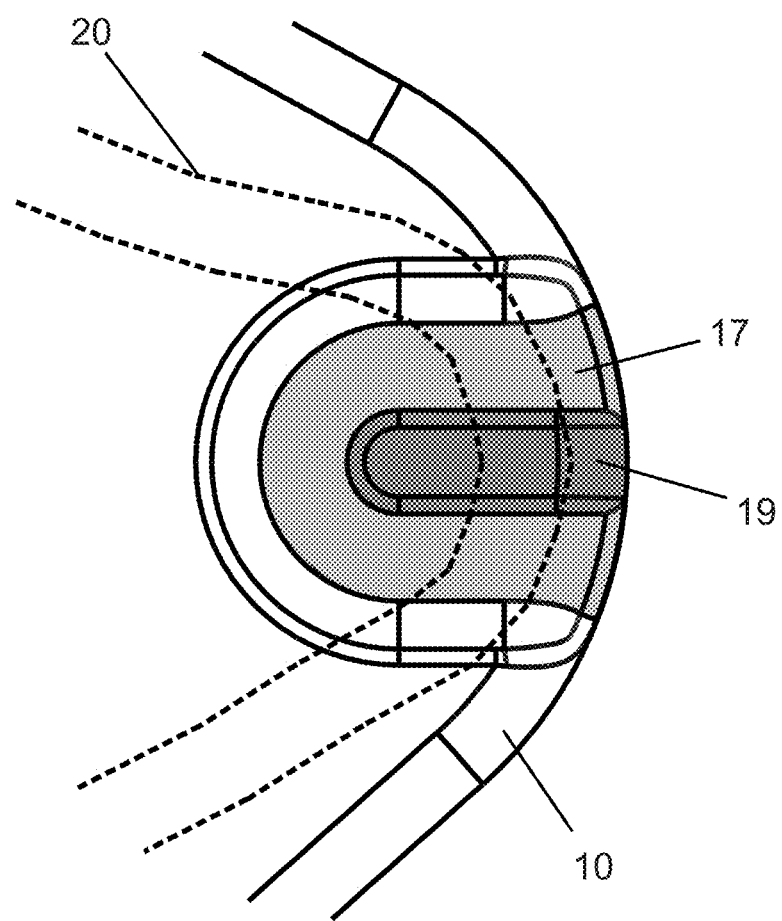
FIG. 24 is an expanded view of the objects of FIG. 23 at location A.
Figure 25:
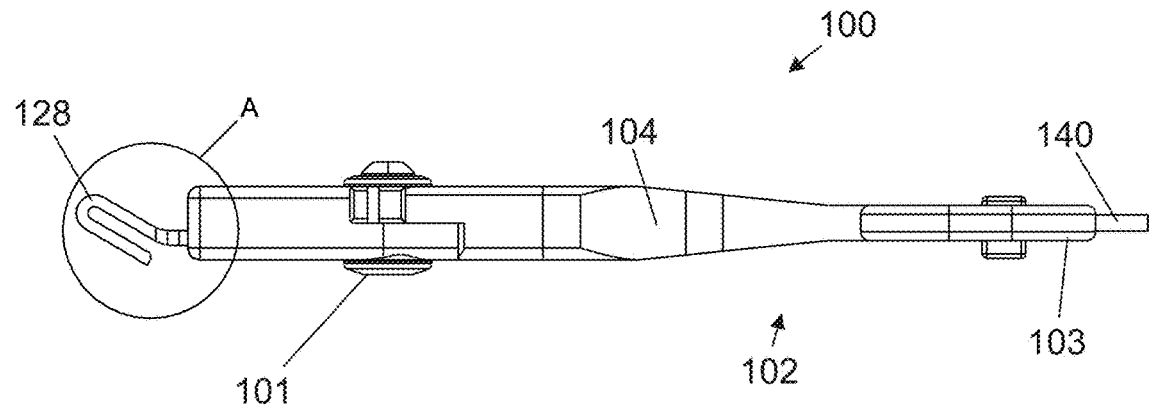
FIG. 25 is a plan view of an alternate embodiment coagulating device (handpiece) suitable for use in connection with the methods of the present invention.
Figure 26:
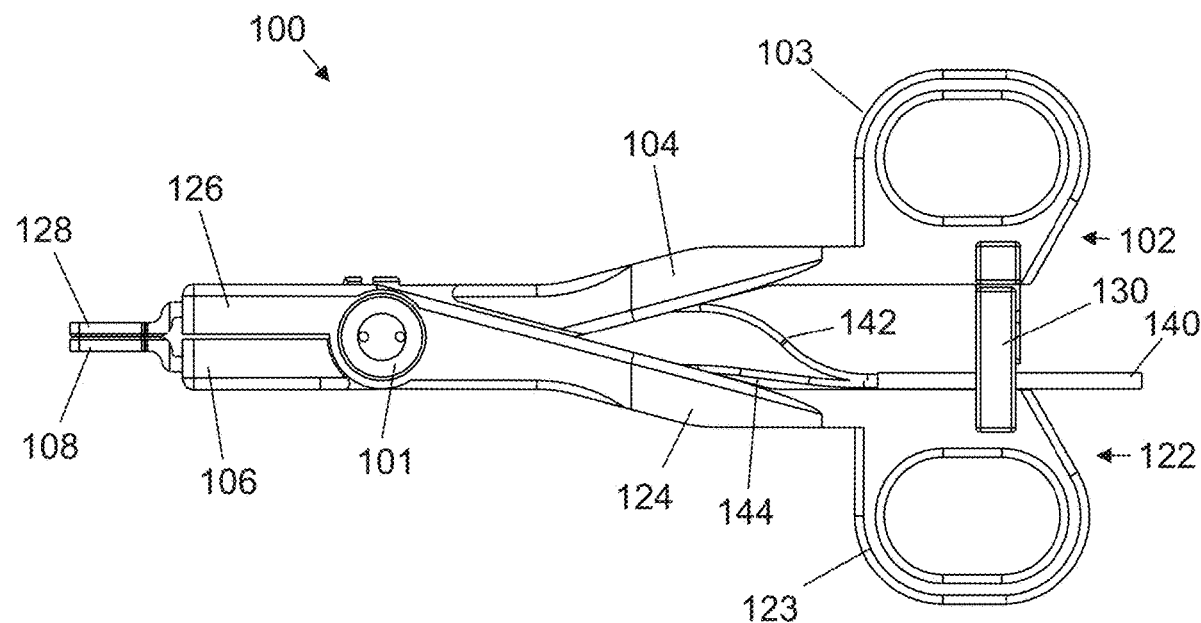
FIG. 26 is a side elevational view of the objects of FIG. 25.

An exemplary procedure for treating varicose veins in accordance with the methods of the present invention is illustrated in FIGS. 14-24. Namely, in a first step, a first varicosed vein is manually identified and isolated in a fold of skin. See FIGS. 14 and 15 wherein vein 20 is located in a fold of skin 10. A local anesthesia is then injected at the treatment site. As shown in FIGS. 16 and 17, clamp 700 is applied to the fold of skin 10 with jaws 718 medial to vein 20 so as to maintain the position of vein 20 in the fold. Thereafter, upper and lower jaws 408 and 428 of handpiece 400 are positioned around distal portions 714 of clamp 700 and handpiece 400 is closed so as to apply compressive force to the tissue between jaws 408 and 428 as shown in FIGS. 18 through 21. The clamping force may be maintained by ratchet element 430 of lower handle assembly 422. Subsequently RF energy from electrosurgical generator 13 (FIG. 7) is supplied to jaws 408 and 428 by wires 442 and 444 and cable 440 so as to coagulate portions of skin 10 and varicose vein 20 that are compressed between jaws 408 and 428. When coagulation is complete, handpiece 400 is removed. The clamp 700 is then removed leaving site 15 as shown in FIGS. 22 through 24. Referring to FIG. 24, site 15 contains region 17 in which skin 10 and vein 20 are sealed by coagulation, and region 19 which remains uncoagulated since it was not compressed between bipolar jaws 408 and 428 of handpiece 400. Region 19 has no blood supply because it is surrounded by coagulated region 17. Because region 19 has no blood supply, it will necrose and slough off thereby dividing vein 20. Tissue adjacent to site 15 will subsequently heal over time. When healing is complete, the gap left by the necrosed tissue will blend into the normal contour of skin 10.

As noted above, in certain instances, the practitioner may elect to actively remove the intervening tissue. Thus, in some embodiments, region 19 is excised as part of the vein treatment procedure. In some of these embodiments, the excision may be accomplished using clamp 700.

In addition to the treatment of varicose veins, methods of the present invention may be applied to the occlusion and division of other swollen, bulging, raised or dilated vessels or ducts within the body of a patient. While handpiece 400 with its bulky pliers-like configuration is particularly well suited for the percutaneous treatment of tissues, accessing other locations within the body of a patient for treatment can be problematic. Accordingly, the present invention contemplates an alternate embodiment handpiece 100 of the present invention that is configured for the treatment of tissue in less accessible locations.

FIGS. 25 through 30 depict alternate bipolar sealing device 100. Bipolar handpiece 100 has an upper handle assembly 102 with a proximal handle portion 104 and a distal portion 106 wherein is mounted lower jaw 108. Upper handle assembly 102 has formed at its proximal end finger loop 103. Handpiece 100 has a lower handle assembly 122 with a proximal handle portion 124 and a distal portion 126 wherein is mounted upper jaw 128. Lower handle assembly 122 has formed at its proximal end finger loop 123. Upper handle assembly 102 and lower handle assembly 122 are rotatably joined by element 101. Lower handle assembly 122 has located adjacent to its proximal end element 130 that, in cooperation with downward extending proximal portion 110 of upper handle assembly 102 maintains the clamping force of jaws 108 and 128, upper surface 132 of element 130 limiting the inter-jaw force that can be applied. Bipolar cable 140 is connected at its proximal end to the bipolar outputs of a suitable electrosurgical generator, and at its distal end, via wires 142 and 144 to upper jaw 128 and lower jaw 108 respectively such that RF energy from the generator is conducted to jaws 108 and 128 so as to coagulate tissue clamped therebetween.

Figure 27:
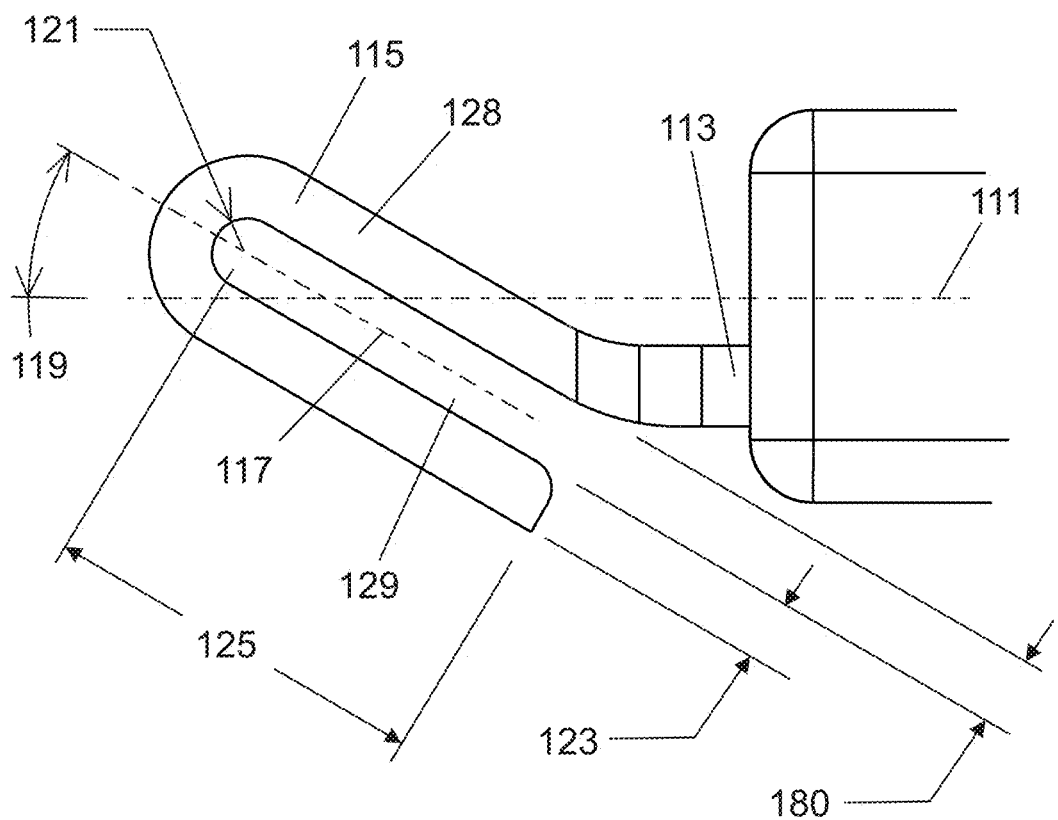
FIG. 27 is an expanded view of the objects of FIG. 25 at location A.
Figure 28:
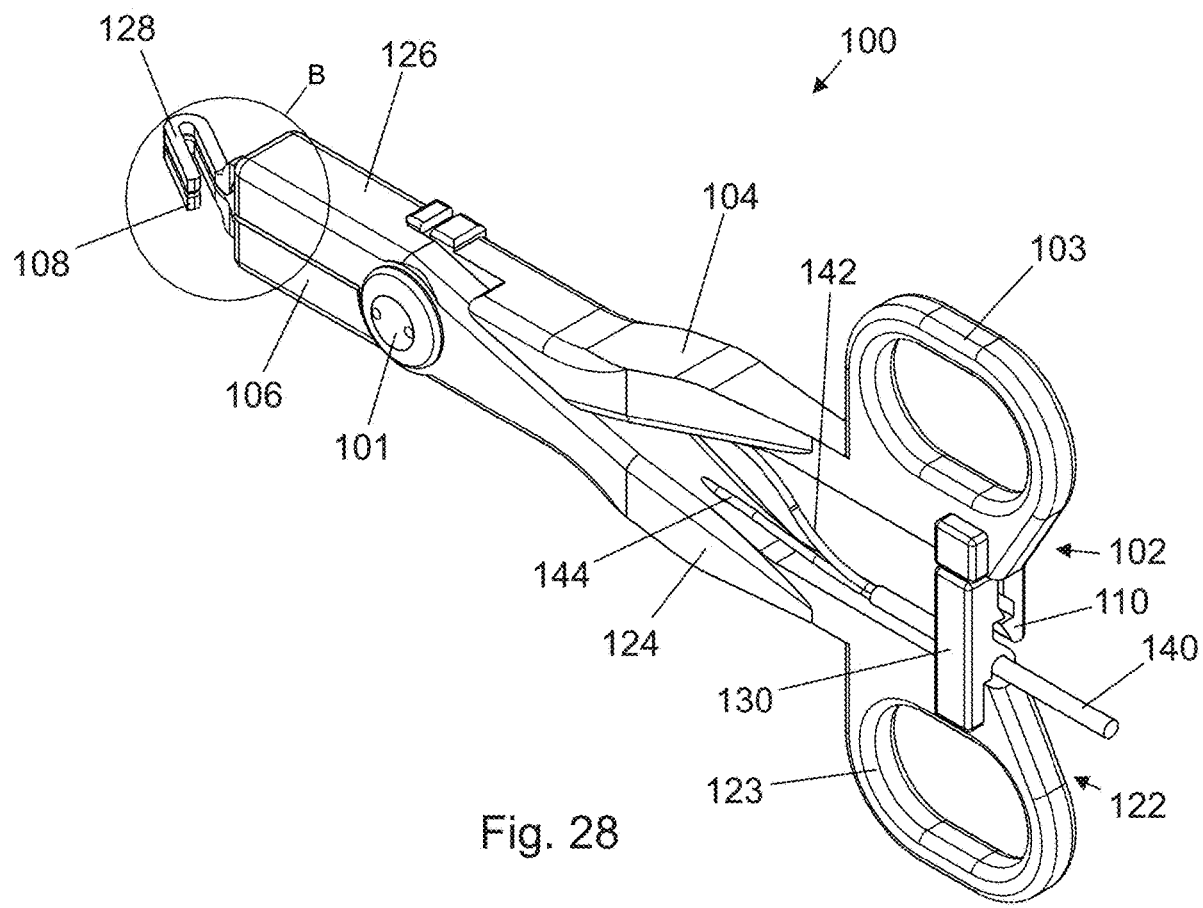
FIG. 28 is a proximal perspective view of the objects of FIG. 25.
Figure 29:
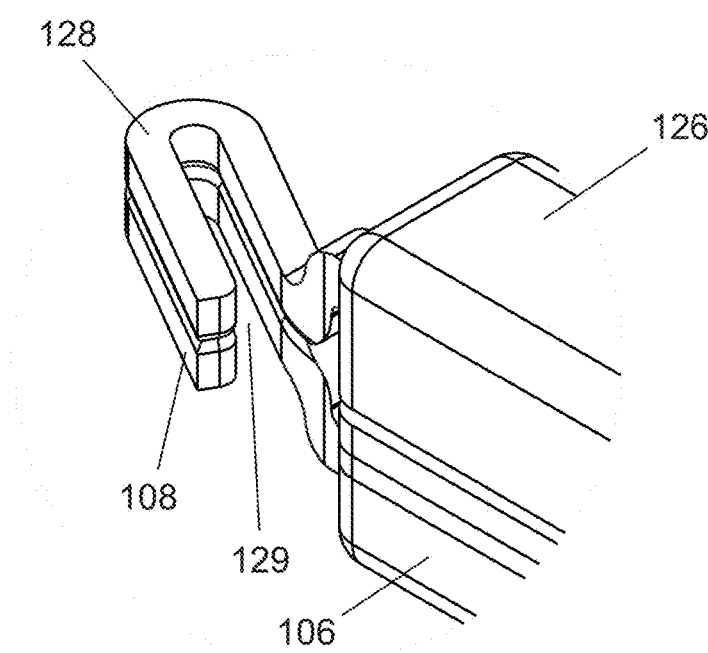
FIG. 29 is an expanded view of the objects of FIG. 28 at location B.
Figure 30:
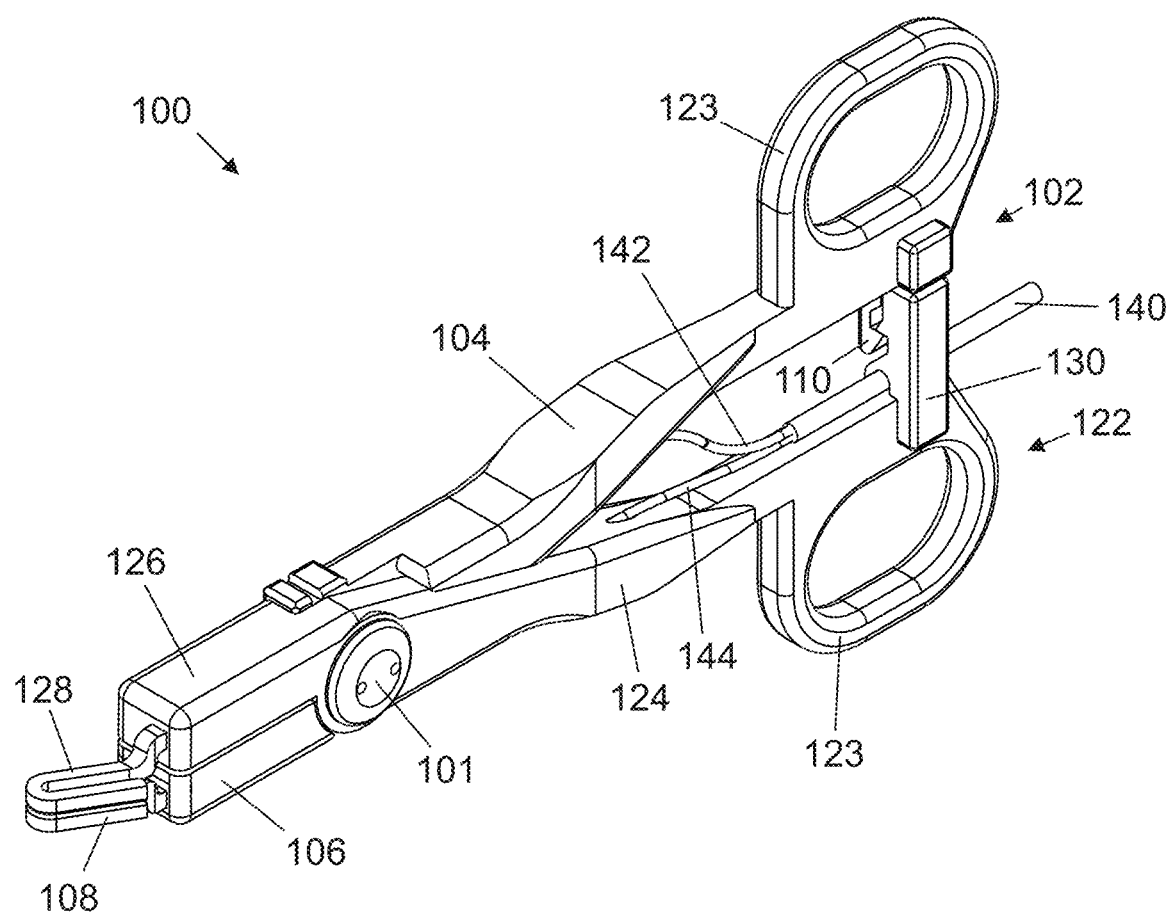
FIG. 30 is a distal perspective view of the objects of FIG. 25.

As best seen in the expanded views of FIGS. 27 and 29, upper 128 and lower 108 jaws are mirror images, each including a proximal portion 113 that attaches to the distal end of the handpiece and a distal portion 115 that is angularly off-set from the longitudinal axis 111 defined by the handpiece, preferably disposed at an angle 119 from the centerline 117 of slot 129. In preferred embodiments angle 119 is between 30 and 60 degrees, optionally between 40 and 50 degrees. This offset angle 119 affords the surgeon better visibility and access to a target surgical site and, as such, angle 119 may be readily optimized for a given application and target location. As best seen in FIG. 27, upper jaw 128 has a "U" shape with a central slot 129 of width 180 and length 125, with lower jaw 108 having a corresponding shape so that tissue may be clamped between the U-shaped jaw portions of jaws 108 and 128. Referring to FIG. 27, the size and relative proportions of slot 180 may be optimized as required for specific applications. Length 125 may be increased or decreased for optimal tissue engagement. Width 180 may be increased or decreased depending on requirements for dividing a duct, and width 123 may be adjusted to achieve an optimal seal width.

Figure 31:
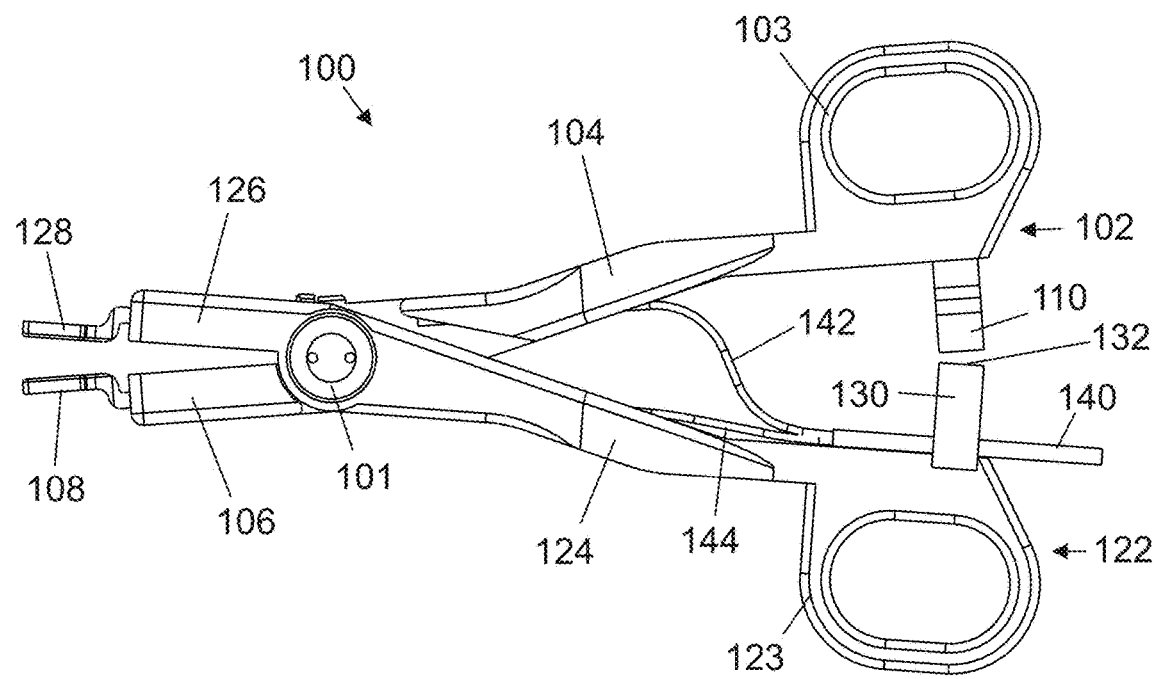
FIG. 31 is a side elevational view of the objects of FIG. 25 with the jaws in an open position in preparation for use.
Figure 32:
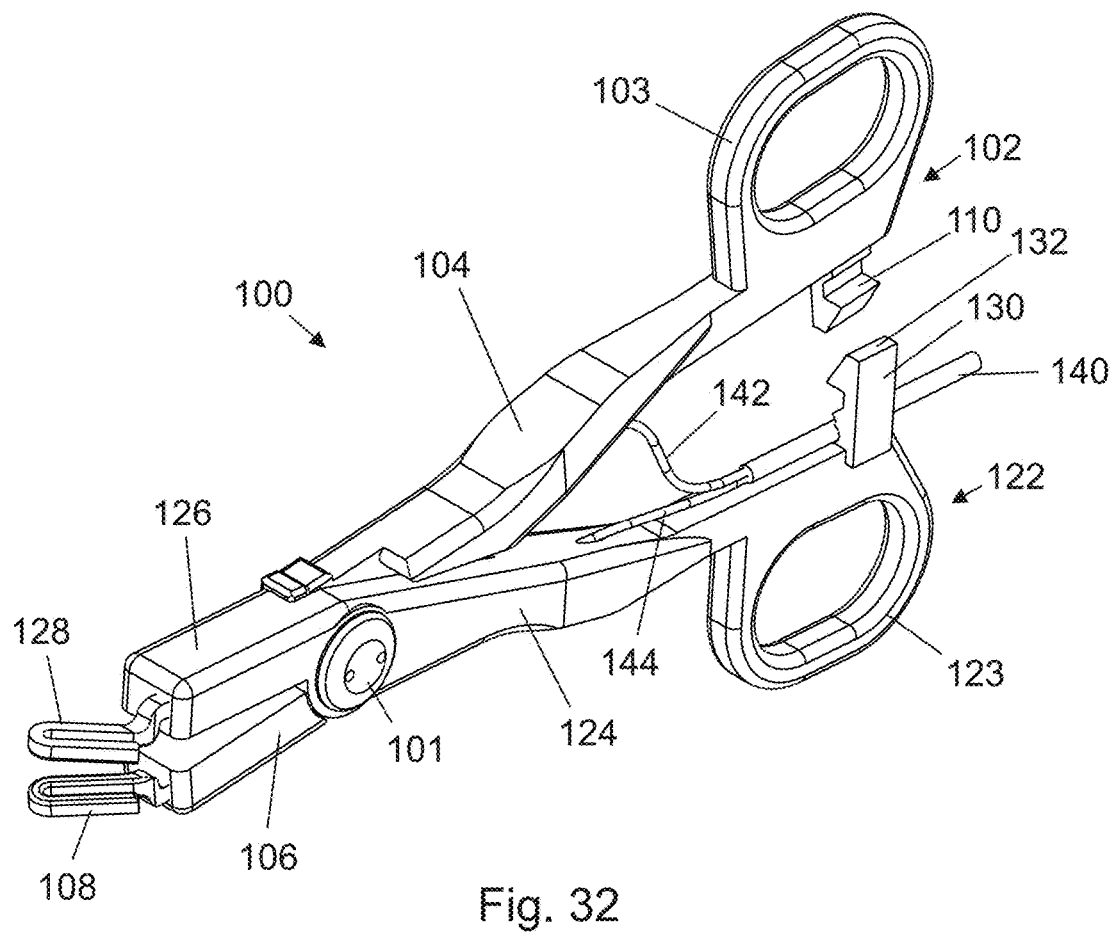
FIG. 32 is a distal perspective view of the objects of FIG. 31.

In FIGS. 31 and 32, bipolar device 100 is depicted in an unclamped condition in preparation for placement of jaws 108 and 128 around clamp 700 or another suitably configured clamping device that is maintaining the percutaneous position of a vessel or duct to be treated (e.g., sealed and divided). In a preferred embodiment, the clamping device is constructed from or coated with a suitable dielectric material as previously described.

Device 100 is used in the same manner as device 400 previously herein described. Namely, a duct (or vessel) requiring occluding and dividing is located and isolated in a fold of skin or surrounding tissue. Isolation of the duct is maintained in the fold by a clamp placed distal to the duct. Jaws 108 and 128 are positioned around the clamp and closed onto the tissue until elements 110 and 130 engage to maintain closure, jaws 108 and 128 exerting a predetermined pressure on the tissue positioned therebetween. The electrosurgical generator is activated causing RF energy to flow between jaws 108 and 128 causing heating of the tissue. This heating, combined with compressive force from jaws 108 and 128 causes sealing of the tissue and occlusion of the duct.

Figure 33:
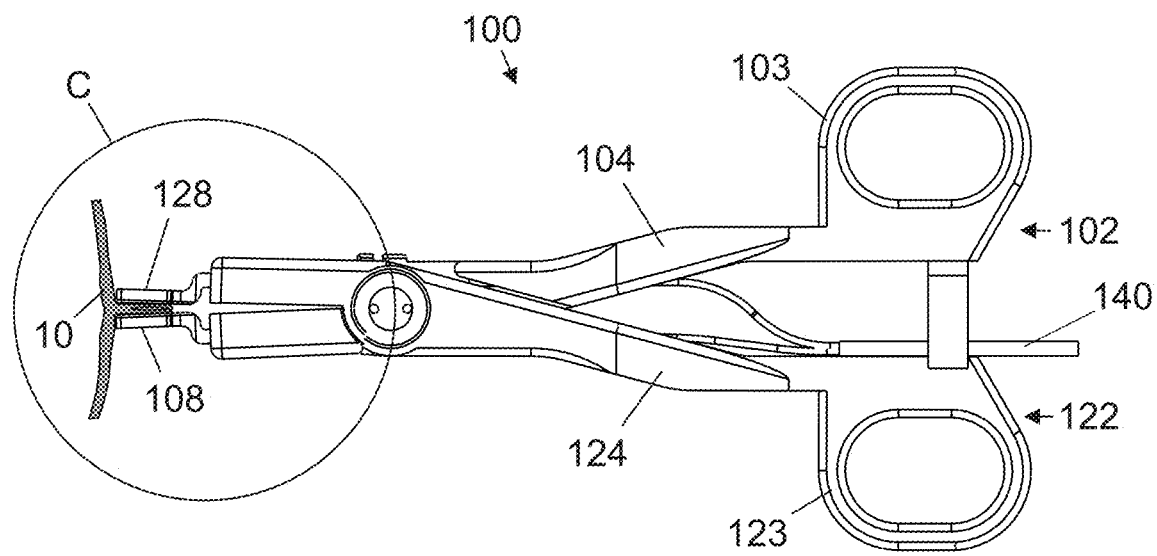
FIG. 33 is a side elevational view of the handpiece of FIG. 25 clamped percutaneously on a duct in preparation for sealing.
Figure 34:
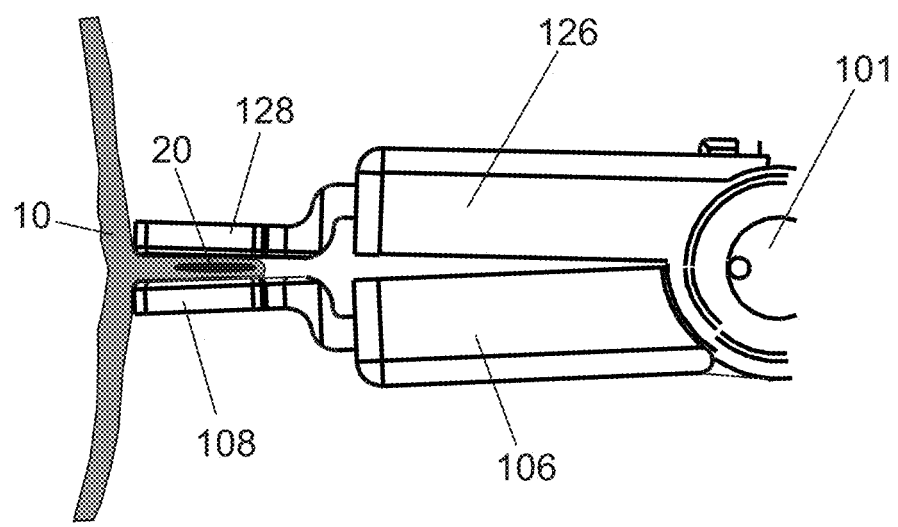
FIG. 34 is an expanded view of the objects of FIG. 33 at location C.

FIGS. 33 and 34 depict bipolar device 100 percutaneously disposed on duct 10 in preparation for sealing by bipolar coagulation. Elements 130 and 110 (see FIG. 28) are engaged so that a predetermined clamping force is applied to tissue 10 and duct 20 between jaws 108 and 128. For clarity, positioning clamp 700 is not shown.

Figure 35:
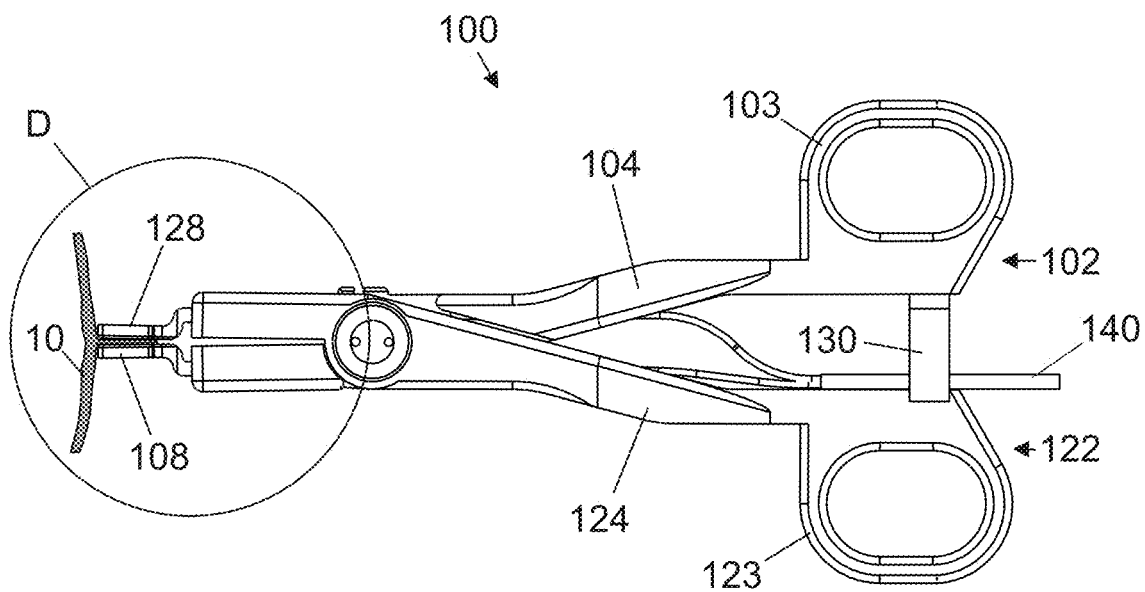
FIG. 35 is a side elevational view of the handpiece and tissue of FIG. 33 with percutaneous sealing of the duct and adjacent tissue complete.
Figure 36:
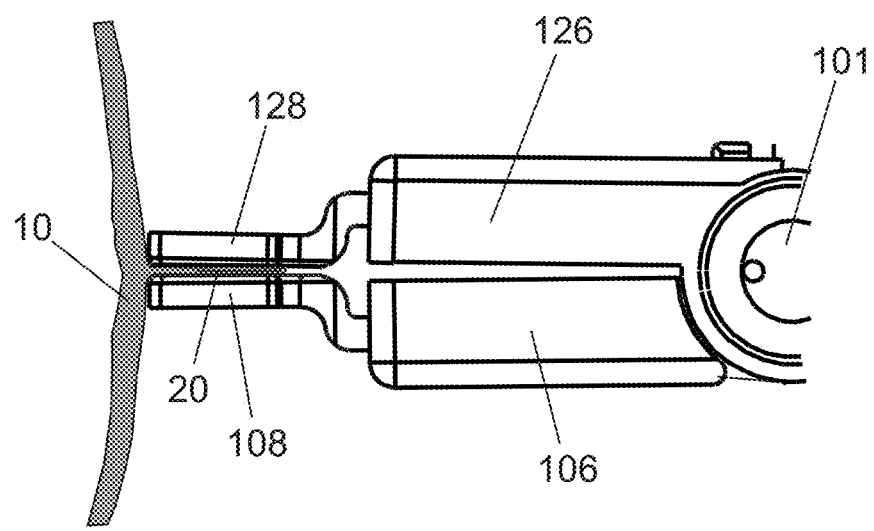
FIG. 36 is an expanded view of the objects of FIG. 35 at location D.

During bipolar sealing, heat is created within tissue 10 and duct 20 by RF energy flowing between jaws 108 and 128. This heat along with compressive force applied to tissue 10 and duct 20 by jaws 108 and 128 causes shrinking of the tissue and the formation of a seal. FIGS. 35 and 36 depict device 100, tissue 10 and duct 20 with sealing completed. The thickness of the tissue between jaws 108 and 128 has been reduced significantly.

INDUSTRIAL APPLICABILITY

While the percutaneous sealing and dividing method has been described with regard to specific embodiments, namely the treatment of varicose veins, it is to be understood that foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. For example, the above-described materials and methods may be readily applied to the treatment of any subcutaneous vein, vessel, or other bulging, swollen, raised or dilated duct in need of sealing, occlusion, and division. To wit:

The methods of treatment previously herein described address the sealing of a single duct or vein. In other treatment methods contemplated by the present invention, a plurality of veins supplying blood to a discrete region may be sealed so as to necrose tissues within that area. For instance, when treating a small tumor, a surgical clamp may be applied to the tumor or distally adjacent to the tumor. The bipolar coagulating jaws may then be positioned around the clamp as previously herein described, with the tumor positioned within the open central slot. Likewise, as previously described, activation of the bipolar jaws can cause the tissue disposed between the bipolar jaws to become coagulated and, in this manner, eliminate downstream blood supply to the tumor and adjacent tissue. Such a lack of a blood supply will cause the tumor to necrose.

In addition, while the above method is described with reference to a tumor, it will be readily apparent to the skilled artisan that any undesirable tissue structure may be treated in this manner. Likewise, the skilled artisan will recognize that the bipolar jaws described herein may be optimally configured to treat a variety of sizes and tissue types. For example, the width and/or length of the central slot may be increased as needed; similarly, the width of the sealing surfaces may be modified to suit a particular application or environment. Tissue structures treated in this manner may be disposed on or accessible via the skin surface or, alternatively, be internal to the body of a patient.

Other uses, advantages and features will become apparent from the claims filed hereafter, with the scope of such claims to be determined by their reasonable equivalents, as would be understood by those skilled in the art. All such applications fall within the scope of this invention. Thus, the invention is intended to be defined not by the above description, but by the following claims and their equivalents.

What is claimed:

1. A method for occluding and dividing a vein, vessel, or duct in need thereof, said comprising the steps of:
   (a) locating a bulging, swollen, raised or dilated length of said vein, vessel, or duct;
   (b) positioning a tissue-capturing distal portion of a surgical clamp about said length of said vein, vessel, or duct located in step (a) so as to temporarily isolate said length;
   (c) providing a coagulating bipolar device having a proximal handle portion that defines a longitudinal axis of said device and an active distal portion characterized by a pair of opposingly-faced, upper and lower coagulating jaws, wherein each of said jaws is (i) movable between open and closed positions, and (ii) provided with mating distal tips and inner edges, whereby, when said jaws are in the closed position and viewed in a plan view, said mating distal tips are angularly offset from said longitudinal axis and said mating inner edges engage to define an interior perimeter comprised of (1) an open central slot that terminates in (2) lateral opening sized to permit said distal clamping portion to be positioned around said tissue-capturing distal portion of said surgical clamp that retains said tissue-capturing distal end of said surgical clamp that retains said length of vein, vessel, or duct located in step (a) and isolated in step (b);
   (d) tightly closing said jaws about the tissue-capturing distal portion of said surgical clamp to thereby define a first area of clamped tissue disposed between said closed jaws and a second area defined by said interior perimeter that includes said isolated length of vein, vessel or duct retained by said tissue-capturing distal portion of said surgical clamp; and
   (e) activating said coagulating bipolar device so as to coagulate said first area of clamped tissue.

2. The method according to claim 1, wherein said locating step (a) further includes the step of percutaneously manipulating said length of said vein, vessel, or duct into a fold of adjacent dermal tissue.

3. The method of claim 1, further including step (f), wherein both said coagulating device and surgical clamp are disengaged from said vein, vessel, or duct.

4. The method of claim 1, wherein said vein, vessel or duct is a varicosed vein.

5. The method of claim 1, wherein vein, vessel or duct is a spider vein.

6. The method according to claim 1, wherein said surgical clamp is a ring forceps.

7. The method according to claim 6, wherein a distal end of said ring forceps is placed about and compressed onto said length of said vein, vessel, or duct.

8. The method according to claim 1, wherein said surgical clamp is a tenaculum.

9. The method according to claim 1, wherein said inner edges of said pair of opposingly-faced, upper and lower coagulating jaws are sharpened so as to enable direct excision of said second area that includes said isolated portion of said vein, vessel, or duct.

10. The method according to claim 1, wherein the coagulation of said first area of clamped tissue serves to occlude and divide the vein, vessel, or duct into separated sealed proximal and distal legs.

11. The method according to claim 10, wherein the coagulation of said first area of clamped tissue further serves to deaden sensory nerves proximate to said first area of clamped tissue.

12. The vasectomy method according to claim 1, wherein said upper and lower jaws as well as said first area of clamped tissue are arcuate in shape such that said second area comprises a convex region.

13. A method for treating varicosed veins in a patient in need thereof, said method comprising the steps of:
   (a) locating a bulging, swollen, raised, or dilated length of a varicosed vein and percutaneously manipulating said length into a surface fold of the patient's skin;
   (b) placing a tissue-capturing distal end of a surgical clamp about said length located in step (a) so as to temporarily isolate said length of the varicosed vein;
   (c) providing a bipolar device having a proximal handle portion that defines a longitudinal axis of the device and a distal clamping portion characterized by a pair of opposingly-faced, upper and lower coagulating jaws, wherein each of said jaws is (i) movable between open and closed positions, and (ii) provided with mating distal tips and inner edges, whereby, when said jaws are in the closed position and viewed in a plan view, said mating distal tips are angularly offset from said longitudinal axis and said mating inner edges engage to define an interior perimeter comprised of (1) an open central slot that terminates in (2) a lateral opening sized to permit said distal clamping portion to be positioned around said tissue-capturing distal end of said surgical clamp that retains said isolated length of the varicosed vein;

(d) tightly closing said coagulating jaws about the tissue-capturing distal end of said surgical clamp to thereby define (i) a first area of clamped tissue disposed between said closed coagulating jaws, and (ii) a convex second area that includes said length of the vein isolated by the tissue-capturing distal end of said surgical clamp; and (e) activating said bipolar device so as to coagulate said first area of clamped varicosed tissue.

14. The method of claim 13, wherein said vein is a superficial tributary vein.

15. The method of claim 13, wherein said vein is a spider vein or thread vein.

16. The method of claim 13, wherein said method further comprising step (f): sliding the tissue-capturing distal end of said surgical clamp relative to the jaws of the bipolar device in a direction normal to a plane defined by said coagulating jaws, whereby outer surfaces perimetral to said tissue-capturing distal end of said surgical clamp interact with the mating inner edges of the coagulating jaws of said bipolar device so as to excise some or all of said second area, including said isolated length of vein, and thereby divide said first area of clamped tissue into two coagulated and sealed proximal and distal ends.

17. The method of claim 16, wherein said method further comprises step (g):
disengaging said upper and lower coagulating jaws from said first area of clamped tissue immediately after step (f).

18. The method of claim 13, wherein said mating distal tips are offset from the longitudinal axis of the device by about 30 to about 60 degrees.

19. The method of claim 18, wherein said mating distal tips are offset from the longitudinal axis of the device by about 40 to about 50 degrees.

20. The method of claim 13, wherein said upper and lower coagulating jaws are arcuate in shape.

21. The method of claim 13, wherein said upper and lower coagulating jaws comprise mirror-image U-shaped curves.

22. The method of claim 13, wherein said mating inner edges of said upper and lower coagulating jaws comprise planar cutting edges and said outer edge surfaces perimetral to said tissue-capturing distal end of said surgical clamp comprise curvilinear sharpened surfaces, whereby said excision of some or all of said second area of the vein tissue, including said isolated length of vein, is achieved through shearing action that arises from engagement of said sharpened curvilinear surface with said planar cutting edges.

* * * * *